United States Patent
Veatch et al.

(10) Patent No.: US 7,341,295 B1
(45) Date of Patent: Mar. 11, 2008

(54) PREHENSOR DEVICE AND IMPROVEMENTS OF SAME

(75) Inventors: Bradley Delton Veatch, Westminster, CO (US); Joseph David Scott, Centennial, CO (US)

(73) Assignee: ADA Technologies, Inc., Littleton, CO (US)

( * ) Notice: Subject to any disclaimer, the term of this patent is extended or adjusted under 35 U.S.C. 154(b) by 261 days.

(21) Appl. No.: 11/036,084

(22) Filed: Jan. 14, 2005

Related U.S. Application Data

(60) Provisional application No. 60/536,667, filed on Jan. 14, 2004.

(51) Int. Cl.
*B25J 15/08* (2006.01)
*A61F 2/54* (2006.01)

(52) U.S. Cl. .......................... 294/106; 294/111; 623/64

(58) Field of Classification Search ............ 623/57–65; 294/106, 104, 111, 99.1; 414/5–7; 901/31, 901/36, 39
See application file for complete search history.

(56) References Cited

U.S. PATENT DOCUMENTS

| | | | |
|---|---|---|---|
| 1,981,698 A | | 11/1934 | Henning |
| 2,098,481 A | | 11/1937 | Baird |
| 2,382,403 A | | 8/1945 | Eberle |
| 2,409,884 A | | 10/1946 | Mollenhour |
| 2,638,604 A | | 5/1953 | Motis |
| 2,641,769 A | | 6/1953 | Robinson |
| 2,710,974 A | | 6/1955 | Motis |
| 3,604,017 A | | 9/1971 | Brown et al. |
| 4,225,983 A | | 10/1980 | Radocy et al. |
| 4,332,038 A | * | 6/1982 | Freeland ....................... 623/64 |
| 4,377,305 A | | 3/1983 | Horvath |
| 4,792,338 A | | 12/1988 | Rennerfelt |
| 4,865,613 A | * | 9/1989 | Rizzo ........................... 623/65 |
| 4,923,477 A | | 5/1990 | Horvath |
| 4,990,162 A | | 2/1991 | LeBlanc et al. |
| 5,116,386 A | | 5/1992 | Scribner |
| 5,219,366 A | | 6/1993 | Scribner |
| 6,010,536 A | * | 1/2000 | Veatch ........................ 623/63 |
| 6,443,032 B1 | | 9/2002 | Fujii et al. |

FOREIGN PATENT DOCUMENTS

| | | |
|---|---|---|
| FR | 488300 | 9/1918 |
| GB | 126 457 | 5/1919 |

OTHER PUBLICATIONS

Abstract for Phase I SBIR Contract, National Institute of Children's Health and Human Development (NICHD) Grant IR43HD39046-01, (publication date unknown), 1 p.

(Continued)

*Primary Examiner*—Dean J Kramer
(74) *Attorney, Agent, or Firm*—Sheridan Ross P.C.

(57) ABSTRACT

A prehensor is provided comprising embodiments of a variable mechanical advantage mechanism, the prehensor including a first mechanical advantage for sizing an object, and a second mechanical advantage for gripping the object. Embodiments of the variable mechanical advantage mechanism include a brake assembly and multiple embodiments of a brakeless assembly. Additionally, multiple embodiments of a selectable voluntary opening/voluntary closing mechanism are provided, whereby a single prehensor can be switched back and forth between a voluntary closing mode and a voluntary opening mode. Additional embodiments include a safety clutch, an improved prehensor tendon, replaceable digits, and self decontaminating digits.

21 Claims, 31 Drawing Sheets

OTHER PUBLICATIONS

Abstract for Phase II SBIR Contract, National Institute of Children's Health and Human Development (NICHD) Grant IR43HD39046-02, (publication date unknown), 1 p.

Armstead, B.H., et al.; "Manufacturing Processes, 7th Ed."; *John Wiley & Sons*, New York, 1977, pp. 269-270.

Atkins, Diane J., et al.; "Comprehensive Management of the Upper-Limb Amputee", Chapters 5, 11 and 18; *New York Springer-Verlag New York, Inc.;* 1989.

Cook, R.D., "Concepts and Applications of Finite Element Analysis, 2nd Ed.", *John Wiley & Sons,* New York, 1981, pp. 483.

Cupo et al.; "Clinical Evaluation of a New, Above-Elbow, Body-Powered Prosthetic Arm: A Final Report"; *Journal of Rehabilitation Research and Development*; vol. 35, No. 4, Oct. 1998; pp. 431-446.

Frey, DD and Carlson, LE, "A Body-Powered Prehensor with Variable Mechanical Advantage"; *Prosthetics and Orthotics International*, 1994, 18, 118-123.

Frey, DD, et al., "Voluntary-Opening Prehensors with Adjustable Grip Force"; *Journal of Prosthetic and Orthotics*; vol. 7, No. 4, Fall 1995, pp. 124-130.

Klopsteg, PE, and Wilson, PD (1968); "Human Limbs and Their Substitutes"; *New York: Hafner Publishing Co.*; pp. 226-229.

Kruit, J, and Cook, JC, "Body-Powered Hand Prosthesis with Low Operating Power for Children"; *Journal of Medical Engineering & Technology*, vol. 13, No. 1/2, (Jan./Apr. 1989), pp. 129-133.

Landsberger, S, et al. "Child Prosthetic Hand Design: No Small Challenge"; *Proceedings of the 1996 Wescon Conference*, Wescon, Los Angeles, CA, 1996:236-240.

LeBlanc, M, et al., "Mechanical Work Efficiencies of Body-Powered Prehensors for Young Children"; *Journal of Children's Prosthetic-Orthotic Clinics*, vol. 27, No. 3, Winter 1992:70-75.

Meeks, D., and LeBlanc, M., "Preliminary Assessment of Three New Designs of Prosthetic Prehensors for Upper Limb Amputees"; *Prosthetics and Orthotics International*, 1988, vol. 12, 41-45.

Melendez, D., and LeBlanc, M., "Survey of Arm Amputees Not Wearing Prostheses: Implications for Research and Service"; *Journal of the Association of Children's Prosthetics-Orthotics Clinics*; vol. 23, No. 3, Autumn 1988; 8 pp.

Northwestern University REP-PRL/Resource Unit, "What Users Want: 1992 Survey and Results," Capabilities, vol. 2, No. 4, Jan. 1993, 15 pp.

Plettenburg, DH and Herder, JL; "Voluntary Closing: A Promising Opening in Hand Prosthetics"; *Technology and Disability*; 15, 2003:85-94.

Rosenbaum DA, "Human Motor Control, 1st Ed."; *San Diego: Academic Press*; 1991:43.

Sears, H., "Evaluation and Development of a New Hook-Type Terminal Device"; *PhD Dissertation Dept. Of Bioengineering*, University of Utah, Jun. 1983.

U.S. Department of Health and Human Services Publication FDA 87-4222; "An Introduction to Medical Device Regulations"; pp. 2-3.

Veatch; "A Combination VO/VC Terminal Device with Variable Mechanical Advantage"; ADA Technologies, Inc.; Littleton, Colorado, Feb. 28, 2004; 5 pp.

\* cited by examiner

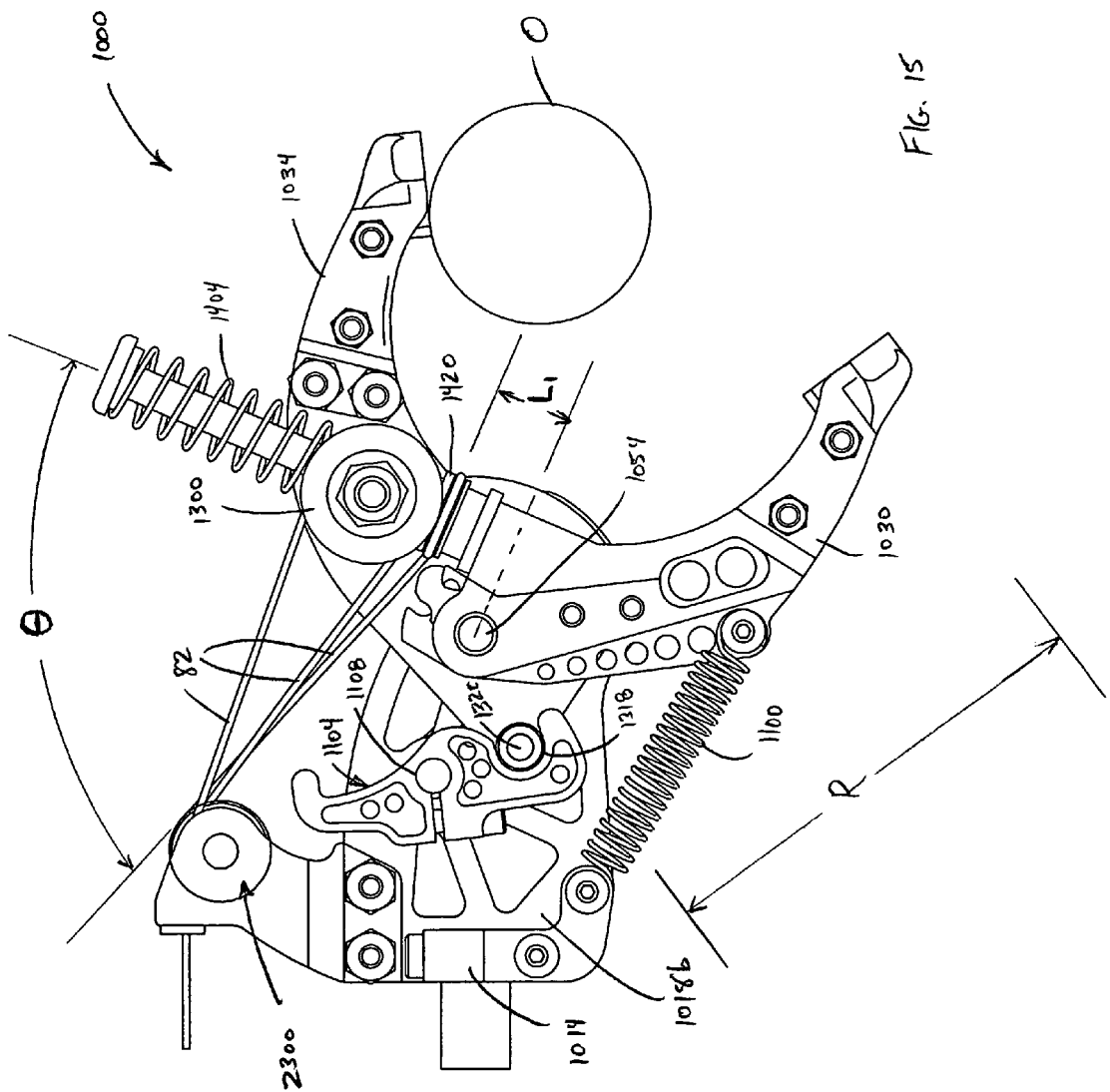

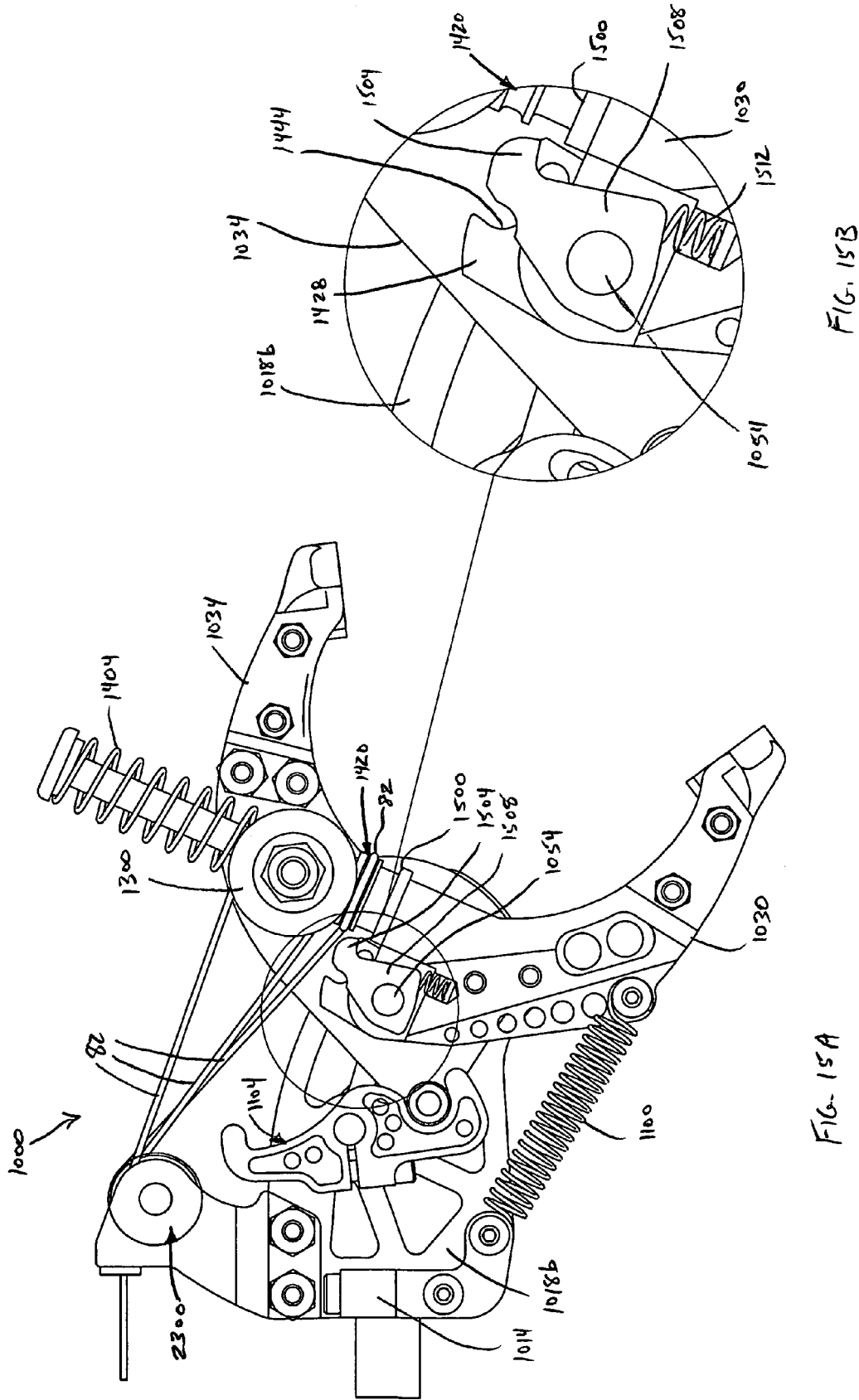

PREHENSOR DEVICE AND IMPROVEMENTS OF SAME

CROSS REFERENCE TO RELATED APPLICATION

The present application claims the benefit of U.S. Provisional Application No. 60/536,667 filed on Jan. 14, 2004, the entire disclosure of which is incorporated herein by reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. Prime Contract ID 2R44 HD39046-02, Contract No. 4553, awarded by the National Institute of Health and National Institute of Child Health and Human Development.

FIELD

This invention relates generally to a prehensor and improvements related thereto, the improvements including embodiments comprising variable mechanical advantage mechanisms, and/or a selectable voluntary opening/voluntary closing mechanism, and/or a safety clutch, and/or a tendon, and/or replaceable digit portions, and/or photocatalytic pads.

BACKGROUND

In the United States, approximately 90,000 individuals are considered to be upper-body amputees, having lost all or a portion of an upper limb. Of those, a subset will use a prosthetic (artificial) arm to enhance or restore their capabilities and, hopefully, their quality of life. While a number of prosthetic devices have been developed to assist these individuals, their use is not wide-spread due, at least in part, to the poor performance and design of existing prosthetics and prehensors. A prehensor, also known as a "gripper" or an "end-effector," is a mechanical grasping device used by an upper-body amputee to serve as an artificial hand.

In response to the need for prosthetic arms and associated prehensors, two types of devices have been developed and marketed: battery-powered electronic systems and body-powered mechanical systems. Electronic systems using a battery package, electric motors, and sophisticated electronic controls have been developed and shown to work reasonably well. Unfortunately, electronic systems are very expensive. In addition, electronic systems can be unrealistically heavy and suffer from inadequate battery life. U.S. Pat. No. 4,792,338 issued to Rennerfelt discloses an electronic or battery-powered prehensor.

The second type of prosthetic devices commonly used are called "body-powered" systems because the wearer controls the system using muscles in his or her body, usually muscles in the shoulder and neck. Body-powered mechanical systems are generally lighter, quieter, and far less expensive than their electronic counterparts, and do not suffer from battery-life limitations.

Within the realm of body-powered prosthetics, there are two primary families of prehensors, differing primarily in their principle of operation. Voluntary opening (VO) prehensors typically include two or more gripping digits (mechanical fingers with rubber pads for friction and better grip) that are held or biased against each other by a spring or one or more strong rubber bands. The wearer moves the digits apart prior to gripping by pulling on a control cable connected to the wearer's shoulder and neck through a harness. When the wearer relaxes or eases the tension on the control cable, the digits close on the object to be held and "grip" it. In essence, voluntary opening prehensors are spring loaded clamps that can be opened at will by the wearer. Therefore, with a voluntary opening prehensor, the wearer's grip on the object is passive and the wearer need do nothing to maintain grip.

Voluntary opening prehensors are popular due to their low cost as compared to electronic prehensors, and the fact that the wearer does not expend energy while gripping an object. Unfortunately, since gripping an object with a voluntary opening prehensor is passive, i.e., the wearer is not expending energy to maintain the grip, the wearer has limited, if any, control over the amount of force exerted on the object. Gripping forces needed to lift heavy objects are excessive for small or lightweight fragile objects. Conversely, the correct gripping force needed to lift a light object will usually be inadequate for heavier objects. U.S. Pat. No. 3,604,017 issued to Brown et al. and U.S. Pat. No. 5,116,386 issued to Scribner disclose voluntary opening prehensors.

The second major type of body-powered prehensors are the voluntary closing (VC) prehensors. As its name implies, unlike a voluntary opening prehensor, the gripping digits in a voluntary closing prehensor are closed upon an object to be grasped by actively exerting force on a control cable attached to the wearer's shoulder and neck using a harness. Voluntary closing prehensors offer several important advantages over voluntary opening prehensors. First, a voluntary closing prehensor is more physiologically intuitive than a voluntary opening prehensor. That is, a voluntary closing prehensor requires a wearer to exert muscular force to grasp and hold an object while a voluntary opening prehensor requires the wearer to relax his or her muscles to initiate and maintain a grip. Second, in a voluntary closing prehensor, the gripping force applied to the object to be grasped by the wearer is directly related to the force the wearer exerts on the control cable. Requiring the wearer to exert force when grasping an object provides feedback to the wearer, thereby giving the wearer a sense of how strong his or her grip is upon the object. This feedback, also called physiological proprioception, allows the voluntary closing prehensor to become an extension of the wearer's body with a natural feel and a confident grasp. Since voluntary opening prehensors do not provide this feedback, the wearer is effectively removed from the gripping cycle. Third, by requiring that the wearer only exert the amount of energy necessary to attain the gripping force required to grasp an object, voluntary closing prehensors conserve a large amount of the wearer's energy. In contrast, voluntary opening prehensors require the wearer to stretch springs or rubber bands to separate or open the digits each time grip is to be applied to an object, regardless of the size or weight of the object. Any excess energy used to open the digits is wasted.

While voluntary closing prehensors are generally more energy efficient than voluntary opening prehensors, voluntary closing prehensors still require the wearer to exert significant energy while maintaining grasp on an object. Therefore, wearers desire voluntary closing prehensors that reduce the energy needed to grasp an object as much as possible while providing feedback as to the force the wearer is exerting against the object. Many types of voluntary closing prehensors are known in the prior art. For example, U.S. Pat. No. 4,225,983 issued to Radocy et al. and U.S. Pat. No. 4,332,038 issued to Freeland both disclose voluntary closing prehensors. Radocy et al. focus their prehensor design towards achieving optimally configured gripping surfaces for the prehensor that can be inexpensively manufactured using stamped plate construction techniques. While Radocy et al. provide a locking pawl to assist the wearer in maintaining a grip on an object, unfortunately, Radocy et al. require that the wearer manually actuate and release the locking pawl, a known safety hazard. Freeland discloses an artificial hand with a pivotal thumb to adapt the hand for gripping different objects. Unfortunately, Freeland does not provide an energy efficient device capable of assisting a wearer in maintaining a grip on an object.

Despite the well developed state of the prior art, there remains a need for a voluntary closing prehensor that conserves the energy expended by the wearer to size and grip an object. Preferably, the voluntary closing prehensor will mechanically assist a wearer in maintaining the grip on the object without requiring any additional manual intervention by the wearer.

To understand the drive problem with current designs, a review of the natural, normal grasp is in order. In execution, the grasp cycle is comprised of two parts: 1) "sizing," where the fingers are brought towards one another to wrap around an object, and 2) "gripping," where force is applied to the object with the fingers to secure it within the hand and thereby permit manipulation. Individuals with their normal hand perform this two-step sequence intuitively, near instantaneously, and subconsciously, permitting the mind to remain focused on high-level aspects of the activity being carried out. Body-powered prosthesis users, in contrast, must consciously generate control cable tension by harnessing unrelated body motions (e.g. scapular abduction, shoulder elevation, elbow flexion); moreover, they can only maintain useful tension levels over relatively short cable excursions.

Average users can develop approximately 2 inches of cable travel and generate approximately 20 lbf cable tension repeatedly without excessive fatigue and discomfort; where tension must be sustained, however, such as for voluntary closing operation, lower values are preferred. Other investigators have suggested that prehensor designs enable users to hold objects up to 3 inches in diameter with tip-pinch forces approaching 12 lbf for reasonable "real world" performance.

A portion of the total available cable excursion must be allotted to each stage of the grasping cycle—sizing and gripping. For two inches of possible cable travel, half of the possible excursion, or 1 inch, is reserved for each part (altering this balance exacerbates the problem described below). In voluntary closing operation, this small excursion must swing the prehensor's moveable digit through its full sizing range of motion to bring it into contact with any size of object within the prehensor—from a sheet of paper to a large bottle—in preparation for the application of gripping force. For the commonly-used digit length of 3.5 inches, the maximum closing angle is computed:

$$3.5'' \left\{ 2\sin\frac{\theta}{2} \right\} = 3.0'' \quad \text{Equation \{1\}}$$

Solving for the sizing angle, θ, we obtain 51°. The tip (where force is actually applied) of a 3.5-inch finger swinging through this angle follows an arc segment having length:

$$\text{arc} length = 3.5'' \left\{ \frac{(51°)\pi}{180} \right\} = 3.1'' \quad \text{Equation \{2\}}$$

This arc length is traversed as the input cable moves through its 1.0-inch excursion, giving an effective mechanical advantage, or forward force ratio (FFR), of 0.32 or less. This ratio emphasizes motion over force, ensuring the drive mechanism can fully close the prehensor from its full open position within the permissible cable excursion limit. Tip force at this ratio is limited to just 1/3 the input cable tension—a relatively low value.

For the second portion of the grasp cycle, gripping, the calculation is simpler. The permissible input tension, 20 lbf (acceptable for short-duration grasping with VC units), should optimally be transformed into at least 12 lbf of tip-pinch force, requiring a FFR of 0.60 or more. Higher mechanical advantage ratios would permit the same grip force to be reached while demanding less muscular exertion. These higher ratios, however, emphasize force over motion, and would hypothetically require nearly 5.2 inches of cable excursion to fully close the device—far beyond that which can be generated through normal harness motions.

A simple mechanical lever arrangement offering only a single, fixed mechanical advantage is inherently incompatible with these opposing functional requirements. That is, it is mechanically impossible for a drive mechanism using a single fixed lever to meet these dual operating requirements.

Some prior art devices attempt to compromise and skirt this functional problem using "average" lever ratios between 0.4 to 0.5, but this sets the device up to deliver poor to marginal performance in both grasping regimes. Fixed-lever systems of this type are attractive because they are mechanically simple and robust, and can be manufactured for low cost. Nevertheless, terminal devices using them are inherently inefficient designs.

Machine theory, i.e. the Chebychev-Grübler-Kutzbach Movability Criterion, requires another degree of freedom be incorporated into the drive mechanism if two mechanical advantages are to be realized-switching lever ratios between grasp cycle stages for example.

Existing prehensor devices are typically configured to provide either a voluntary opening mode of function or a voluntary closing mode of function. Voluntary closing devices, as the name implies, close as the user increases tension in the control cable actuating the unit. Voluntary opening devices, in contrast, also use an actuation cable, but close as the user relaxes their tension. With voluntary opening, cable tension vanishes when the user fully relaxes; grasp may be sustained, however, without fatigue. Large gripping forces and proprioceptive feedback make voluntary closing units desirable and intuitive to operate, but when not engaged in grasp, they are open with the digits apart, making them prone to strike doorframes, furniture, and the user's thigh. Moreover, existing individual voluntary opening or voluntary closing devices do not allow the wearer to changes modes between the functions. That is, wearers are left with a choice of using a voluntary closing mode prehensor, using a voluntary opening mode prehensor, or constant labor-intensive exchanges between two units. Accordingly, it would be advantageous to provide a single prehensor that can be switched back and forth between a voluntary opening and voluntary closing mode of function.

There is also a need for a safety device that releases the closed digits if the separation force on the digits becomes great enough. For example, if a user were to fall while wearing a prehensor gripped to a railing, the user may suffer significant bodily harm if the prehensor were to maintain grasp of the railing throughout the entire event of the user falling. Thus, it would be advantageous to provide a prehensor having a built in safety mechanism that automatically releases the prehensor digits, if necessary.

In addition, there is also a need for a prehensor cable that provides high tensile strength with low frictional characteristics that can be used on sheaves or pulleys with relatively small radii of curvature. Existing cables fabricated from steel or other metal alloys do not possess these qualities.

There is also a need for a prehensor that includes digits that are replaceable if a digit is damaged or the user desires to change it for a new one. More particularly, users of prehensor devices sometimes damage the digits of their prehensor device by, for example, scraping, bending, or burning at least a portion of a digit. Digits are also frequently and permanently soiled and degraded by common chemicals, such as gasoline and cleansers. Accordingly, a need exists to provide digits that can be replaced relatively easily.

There is also a need for the prehensor to incorporate self-sanitizing technology. More particularly, under a variety of circumstances, the digits of a prehensor may be exposed to or become contaminated with unsanitary matter. Accordingly, it would be advantageous to provide prehensor digits that incorporate a self-sanitizing feature.

SUMMARY

In accordance with embodiments of the present invention, a prehensor is provided that includes a variable mechanical advantage mechanism that allows the device to be operated in a first mechanical advantage for grasping or sizing and object, and then provides a second mechanical advantage for gripping. The first mechanical advantage therefore, pertains to moving the closing digit to grasp the object between the digits, and the second mechanical advantage pertains to applying a higher force or gripping force for squeezing the object tighter between the digits. In accordance with embodiments of the present invention, the variable mechanical advantage mechanism comprises a rotatable brake assembly. In accordance with other embodiments of the present invention, the variable mechanical advantage mechanism comprises a rotatable biasing member.

Embodiments of the present invention also optionally include a selectable voluntary opening and voluntary closing mechanism, where the mode of operation of the device may be switched from a voluntary closing mode to a voluntary opening mode, and vice versa. In accordance with embodiments of the present invention, the selectable voluntary opening and voluntary closing mechanism comprises a cam switch that is rotated from a first position to a second position, thus switching modes of operation. In accordance with other embodiments of the present invention, a latch is rotated to change the device from one mode to the other.

In accordance with other embodiments of the present invention, a safety clutch is provided, where the safety clutch acts as an overload protection device that releases the digits from an object if sufficient force is applied between the closed digits. Once excess torque is relieved through slippage, the clutch re-seats undamaged and is again ready for continued service.

In accordance with still other embodiments of the present invention, the digits may include a replaceable digit portion to facilitate providing a replaceable end portion without having to dismantle the prehensor to replace the digit. More particularly, a digit may include an end portion that can be easily removed and replaced with a substitute end portion.

In accordance with other embodiments of the present invention, the digits may include a self-decontaminating material. More particularly, the prehensor may comprise components, such as the digits, that include a photo-catalytic agent that kills bacteria and viruses. In one embodiment, the photo-catalytic agent comprises titanium dioxide.

In accordance with yet other embodiments of the present invention, a tendon is provided that includes a low friction exterior jacket and a high tensile strength, low-creep interior core. The tendon is used within the prehensor, and facilitates rotation of the digits.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 5A is a detail view of a portion of the device shown in FIG. 5;

FIG. 15 is a side elevation view of the device shown in FIG. 10, excluding some components for clarity, wherein the device is in voluntary closing mode with the closing digit fully opened;

FIG. 15A is another side elevation view of the device shown in FIG. 15, excluding some additional components for clarity, wherein the device is in voluntary closing mode with the closing digit fully opened;

FIG. 15B is a detail view of a portion of the device shown in FIG. 15A;

FIG. 21A is a detail view of a portion of the device shown in FIG. 21A;

DETAILED DESCRIPTION OF THE INVENTION

Variable Mechanical Advantage

Figure 1:
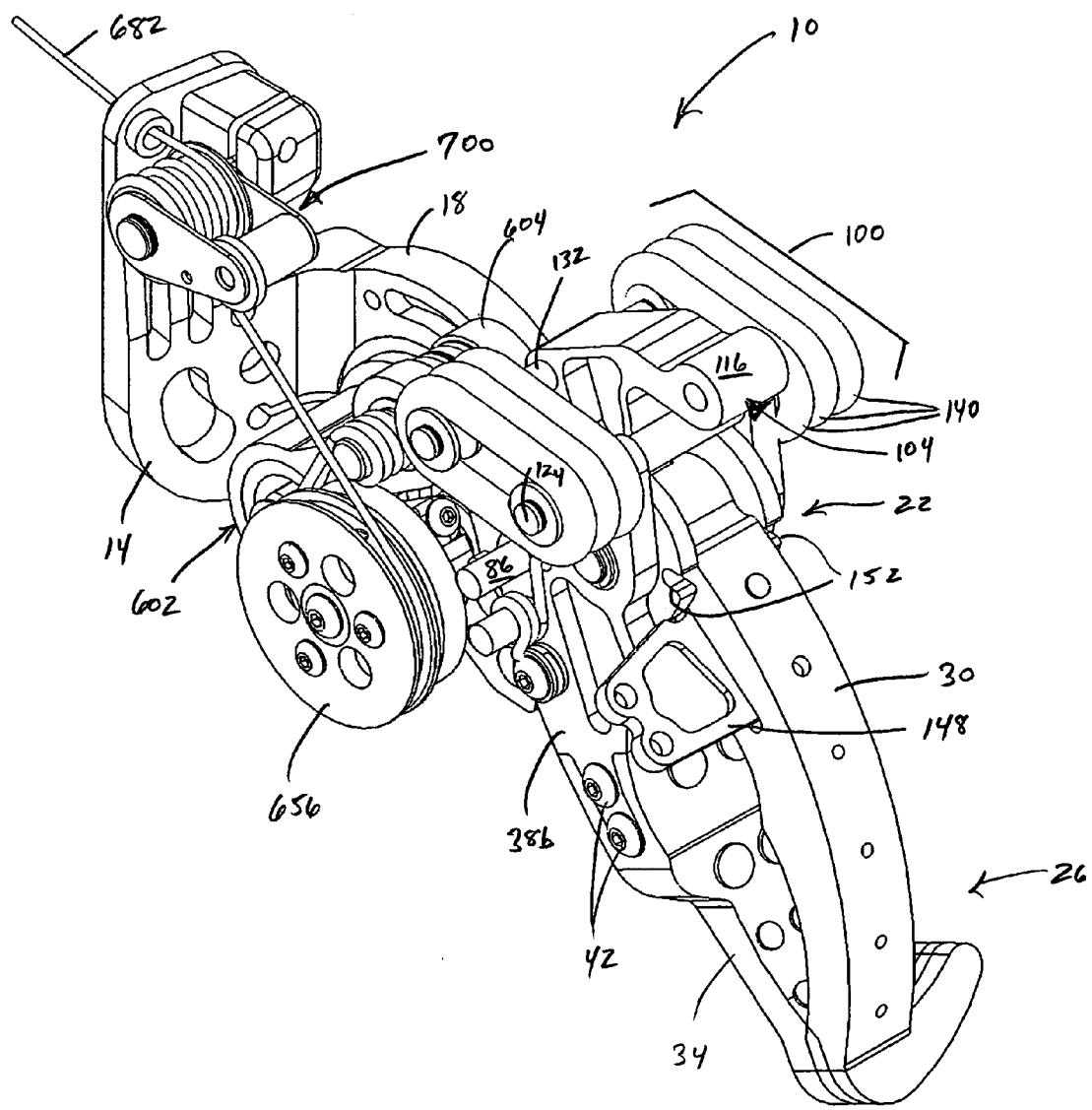
FIG. 1 is a perspective view of a first embodiment of the present invention.
Figure 2:
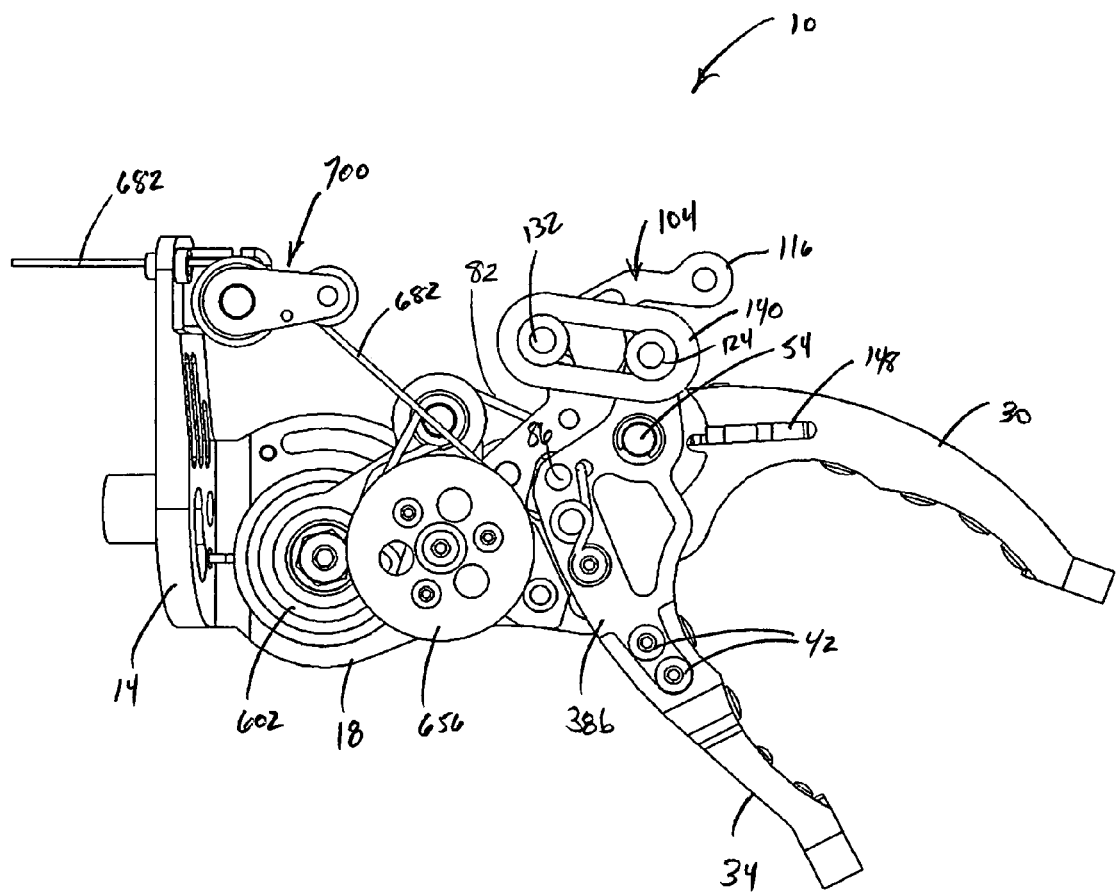
FIG. 2 is a side elevation view of the device shown in FIG. 1.
Figure 3:
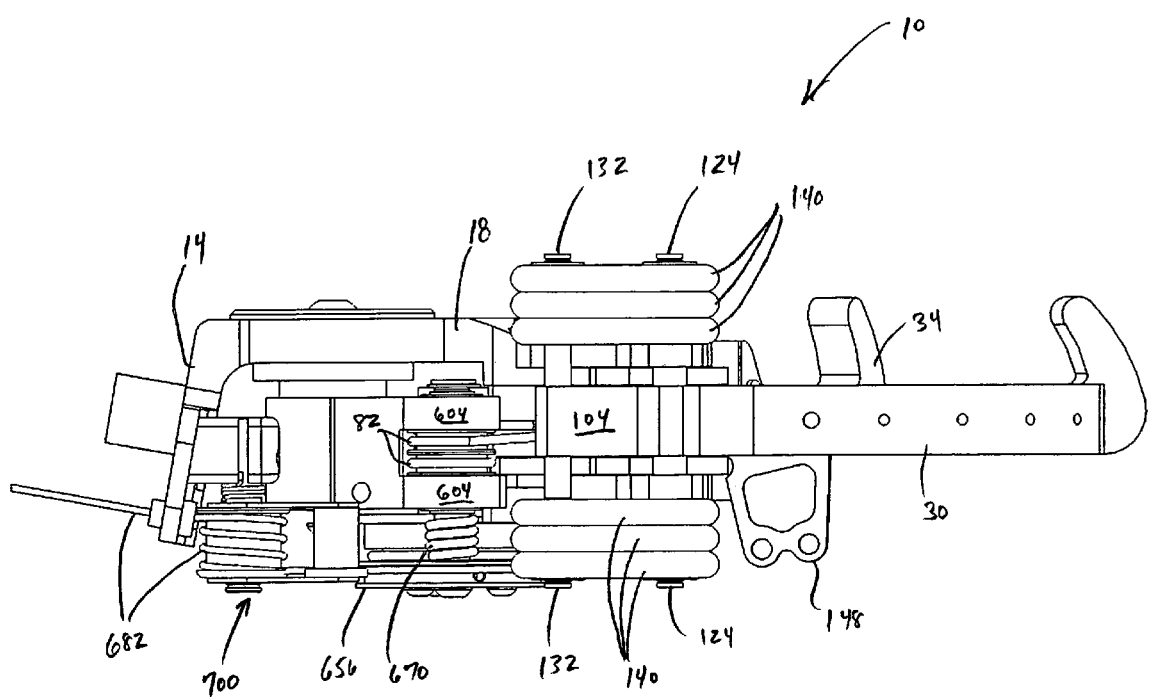
FIG. 3 is a top plan view of the device shown in FIG. 1.

In accordance with embodiments of the present invention, a prehensor device may include a variable mechanical advantage (also referred to herein as "VMA") mechanism. As described below, the VMA mechanism may comprise a brake assembly, or alternatively, the VMA mechanism may comprise a brakeless assembly. Both the brake and brakeless assemblies take energy they receive from the user as cable input, (i.e., force and displacement), and transform it into either: (1) low-force/high-displacement output used to adjust the space between the prehensor digits; or (2) high-force/low-displacement output to provide large traction forces to objects squeezed by the digits.

VMA with Brake Assembly

The following paragraphs describe a prehensor device that utilizes a brake assembly interconnected to the prehensor to provide a mechanism for allowing a user of the prehensor to first grasp an object and then apply a tighter gripping force. The brake assembly is the mechanism that allows the user to first advance the digits of the prehensor to grasp, and then subsequently also apply higher gripping forces because the brake assembly converts the input cable tension into both grasping motion and tighter gripping pressure.

Referring now to FIGS. 1-5A, a prehensor 10 in accordance with embodiments of the present invention is illustrated. The prehensor 10 preferably includes a base member 14 that serves as a mounting plate for interconnecting the prehensor 10 to a prosthetic attachment or harness device (not shown) operatively associated with a portion of the body of the user, such as the user's arm. Alternatively, the prehensor 10 may be interconnected to a robot or robotic device. Interconnected to the base member 14 is a longitudinal member 18. In accordance with embodiments of the present invention, the base member 14 and longitudinal member 18 may be formed of a single piece of material.

The longitudinal member 18 includes a distal region 22 that is interconnected to the digits 26 of the prehensor 10. The digits 26 preferably include a closing digit 30 and an opening digit 34. For the embodiment shown in FIGS. 1-5A, the opening digit 34 preferably includes an opening digit forked portion 38 at the rear portion 40 of the opening digit 34. The opening digit forked portion 38 is configured for interconnecting rear portion 40 of the opening digit 34 to the distal region 22 of the longitudinal member 18. The opening digit forked portion 38 may comprise a plurality of pieces. For example, as shown in FIG. 5, in one embodiment the opening digit forked portion 38 includes a first opening digit forked member 38a and a second opening digit forked member 38b, where upon assembly, the second opening digit forked member 38b is interconnected to the first opening digit forked member 38a using one or more connectors 42, such as rivets, pins, clamps, screws, as well as bolts, their associated nuts, and flat and lock washers.

Figure 4:
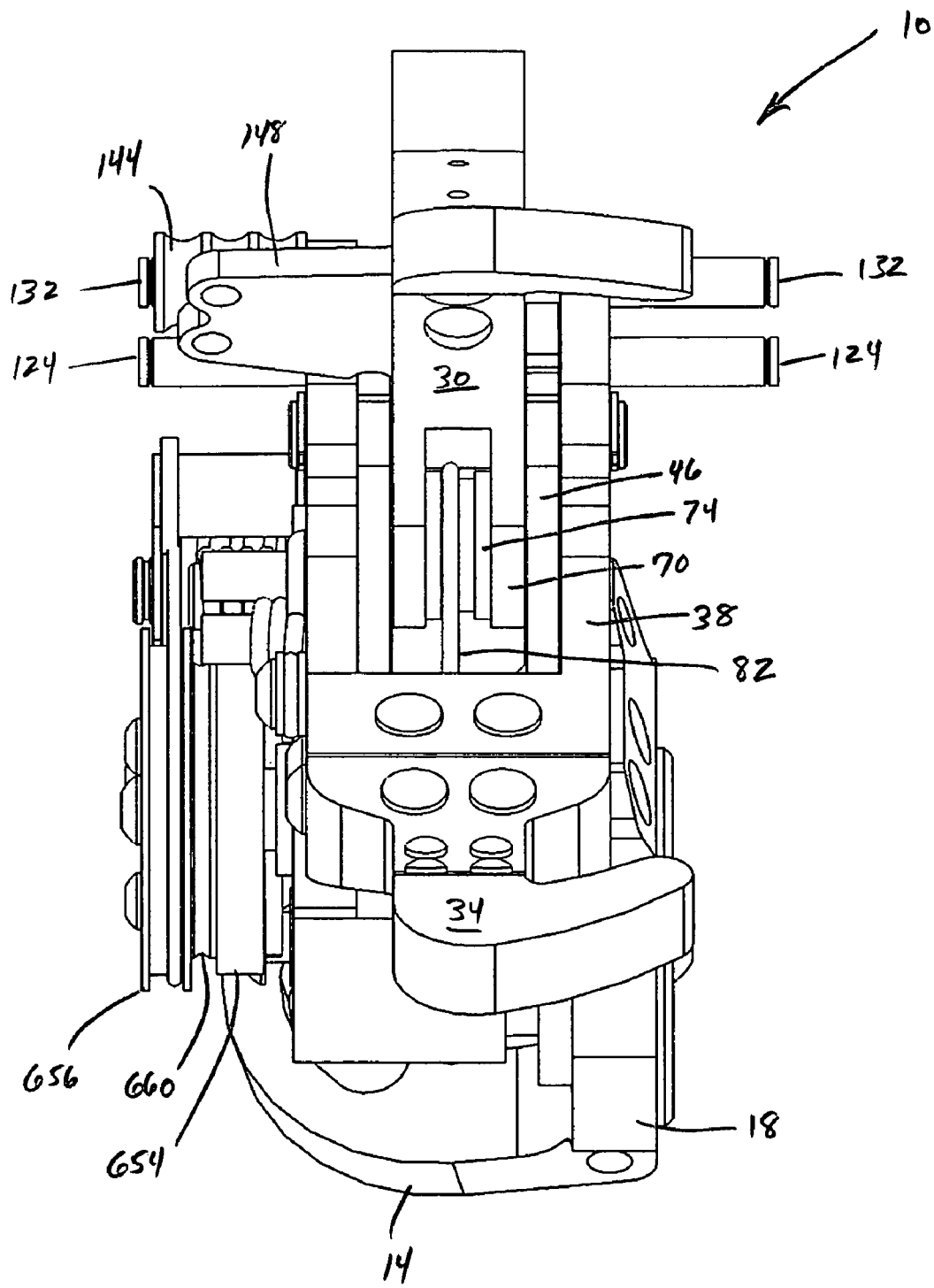
FIG. 4 is a front elevation view of the device shown in FIG. 1, but without tension bands.
Figure 5:
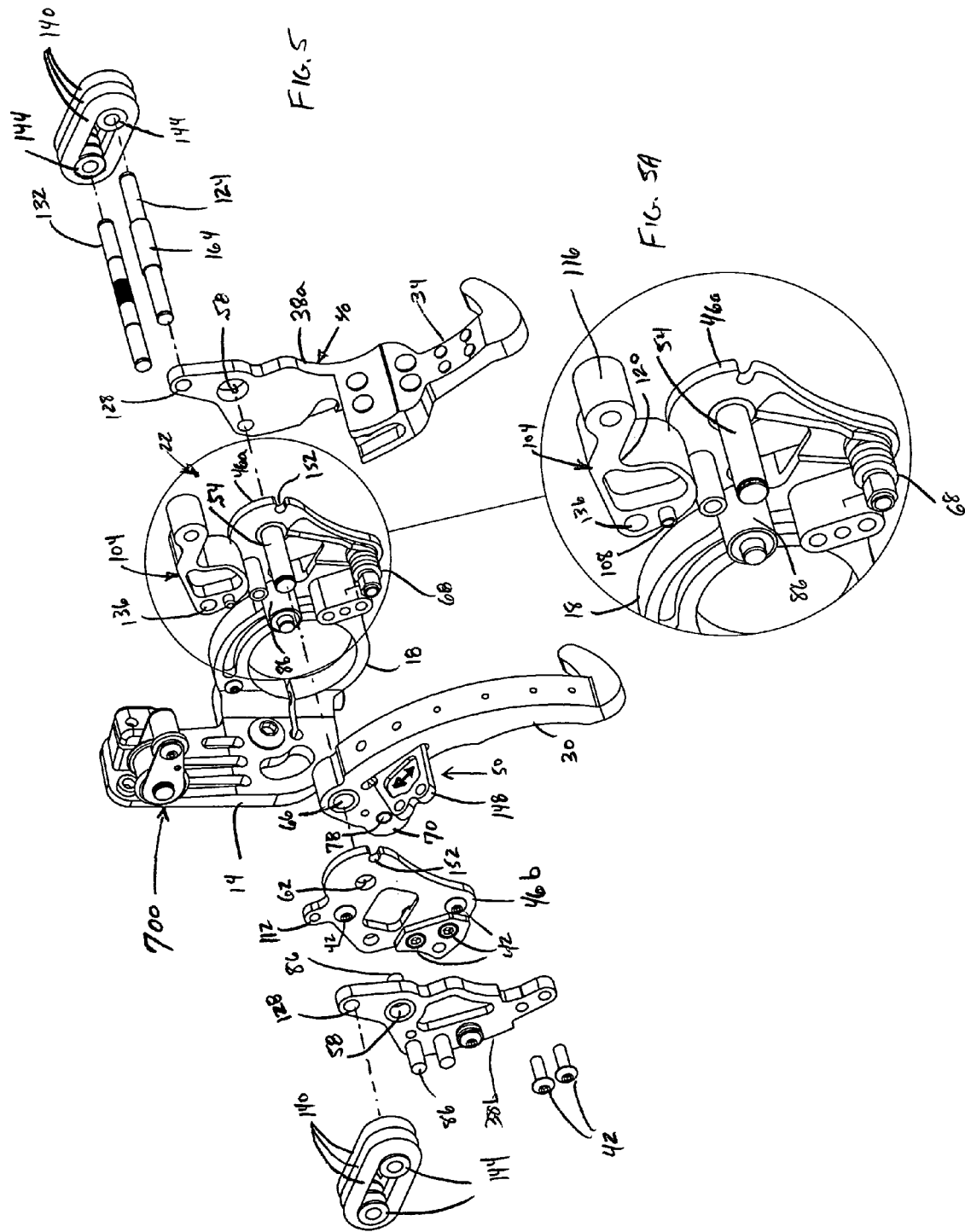
FIG. 5 is a partial exploded perspective view of some components of the device shown in FIG. 1.

For the embodiment shown in FIGS. 1-5A, the opening digit forked portion 38 is situated to the exterior of the longitudinal member forked portion 46 which comprises part of the distal region 22 of the longitudinal member 18. As with the opening digit forked portion 38, the longitudinal member forked portion 46 may comprise a plurality of pieces. For example, as shown in FIG. 5, in one embodiment the longitudinal member forked portion 46 includes a first longitudinal forked member 46a and a second longitudinal forked member 46b, where upon assembly, the second longitudinal forked member 46b is interconnected to the first longitudinal forked member 46a using one or more connectors 42, such as bolts or screws.

Positioned within the longitudinal member forked portion 46 resides the closing digit rear portion 50 of the closing digit 30. Common axle 54 passes through opening digit bore 58 of the opening digit forked portion 38, through longitudinal member bore 62 of the longitudinal member forked portion 46, and through the closing digit bore 66 of the closing digit rear portion 50. When rotated, such as by opening or closing the digits 30 and 34 of the prehensor 10, both the closing digit 30 and the opening digit 34 pivot about the common axle 54. A biasing member or closing digit return spring 68, such as a torsion spring, is preferably located between the longitudinal member forked portion 46, and serves to return the closing digit 30 to its fully open position when the input cable 682 is at rest.

Figure 8:
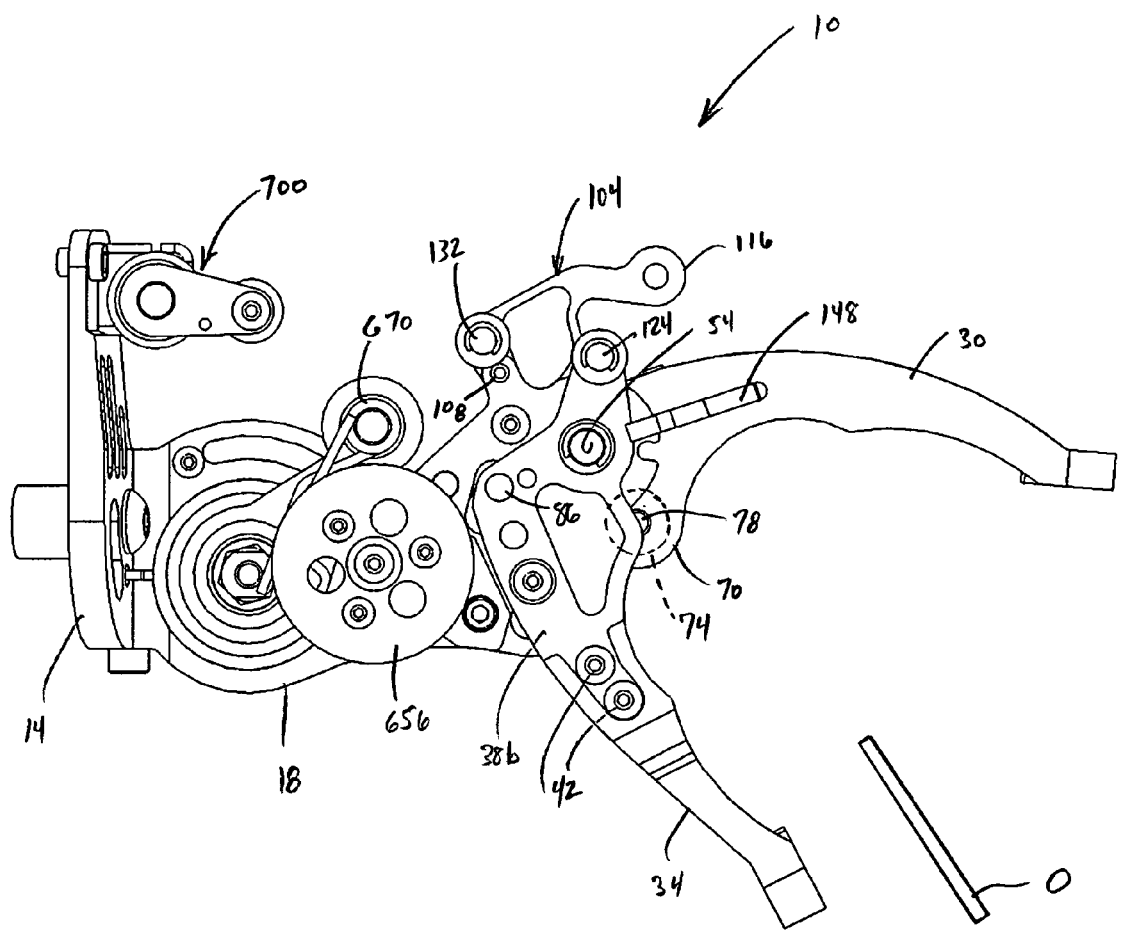
FIG. 8 is a side elevation view of the device shown in FIG. 1, excluding the input cable and tendon for clarity, wherein the device is in voluntary closing mode with the closing digit fully opened.

In accordance with embodiments of the present invention, and as best seen in FIGS. 4 and 8, the closing digit rear portion 50 preferably includes a device 70 that includes a pulley 74 mounted by a pulley axle 78. In use, a user typically interconnects a harness (not shown) having a Bowden cable (not shown) to the prehensor 10. The Bowden cable is then interconnected to a tendon 82 within the prehensor 10. One or more input cables may be used to operatively interconnect the Bowden cable to the tendon 82. The tendon 82 is used to move one or more of the digits 26. In accordance with embodiments of the present invention, a portion of the tendon 82 is wrapped around the pulley 74 of the closing digit 30. To facilitate tension and routing of the tendon, additional tendon guide structures 86 may be provided, such as guide axles or guide pulleys that are incorporated into the distal region 22 of the longitudinal member 18, and/or into the rear portions 40 and 50 of the opening digit 34, and closing digit 30, respectively.

Figure 6:
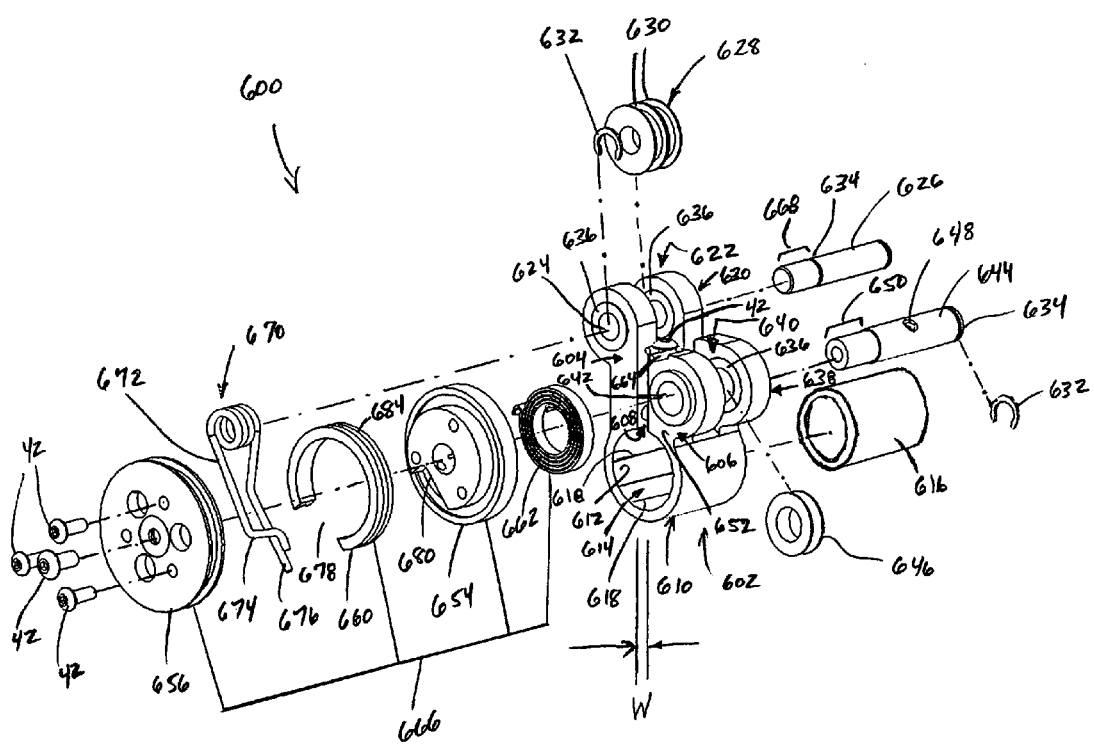
FIG. 6 is an exploded view of a brake assembly in accordance with embodiments of the present invention.

Referring now to FIG. 6, in accordance with embodiments of the present invention, a brake assembly 600 is provided. The brake assembly 600 includes a brake member 602 resembling a U-shape with a first leg 604 and an opposing second leg 606. The first leg 604 is separated from the second leg 606 by a slot 608. The first leg 604 and the second leg 606 may be different lengths, as shown in FIG. 6. The brake member 602 further includes a substantially cylindrical chamber 610 at the base of the first leg 604 and second leg 606. The cylindrical chamber 610 has a substantially cylindrical inside surface 612.

The brake member 602 is deformable such that first leg 604 and second leg 606 can be compressed toward each other. More particularly, depending upon the material type or types used and the dimensions of the legs 604 and 606 of the brake member 602, the brake member 602 is deformable such that either the first leg 604 can be moved toward the second leg 606, or the second leg 606 moved toward the first leg 604, or both legs 604 and 606 moved toward each other simultaneously, thereby reducing the initial width W of the slot 608. The brake member 602 acts a clamp, thereby reducing the diameter of bore 614. As will be described in more detail below, upon reducing the diameter of bore 614, the substantially cylindrical inside surface 612 forming bore 614 squeezes against a substantially cylindrical drum 616 that is interconnected to longitudinal member 18. The cylindrical inside surface preferably includes a plurality of grooves 618 for hydraulically relieving pressure from excess lubricant, such as sewing machine oil, during operation of the brake assembly 600.

The distal end 620 of the first leg 604 includes means for guiding the tendon 82. For the embodiment shown in FIG. 6, the means for guiding the tendon 82 at the distal end 620 includes a first leg forked portion 622 and a first leg bore 624 for receiving a first leg axle 626. The first leg axle 626 preferably retains two adjacent rotatable independent pulleys 628 within the first leg forked portion 622, where the slots 630 of the rotatable independent pulleys 628 are for receiving the tendon 82. As shown in FIG. 6, the first leg axle 626 may be retained within the first leg bore 624 by a clip ring 632 that is received in clip ring groove 634 of first leg axle 626. On either side of the first leg forked portion 622, a cylindrical bearing or bushing 636 is preferably located between the first leg axle 626 and the inside wall of the first leg bore 624.

The distal end 638 of the second leg 606 also includes means for guiding the tendon 82. For the embodiment shown in FIG. 6, the means for guiding the tendon 82 at the distal end 638 of the second leg 606 includes a second leg forked portion 640 and second leg bore 642 for receiving a second leg axle 644. The second leg axle 644 retains a rotatable single slot pulley 646 within the second leg forked portion 640. The second leg axle 644 may include a means for retaining the tendon 82, such as hole 648 through which the tendon 82 may be passed and tied-off. Alternate means for retaining the tendon to the second leg axle 644 are within the scope of the invention, and include a screw or clamp. In accordance with embodiments of the present invention, the tendon 82 preferably starts tied, clamped or otherwise attached to second leg axle 644, then wraps around one of the slots 630 of the two independent pulleys 628 on the first leg axle 626, then wraps around the single slot pulley 646 on the second leg axle 644, then returns to wrap around the second unused slot of the two independent pulleys 628, then extends to wrap around the pulley 74 of the closing digit 30.

As shown in FIG. 6, the second leg axle 644 may be retained within the second leg bore 642 by a clip ring 632 that is received in clip ring groove 634 of second leg axle 644. On either side of the second leg forked portion 640, a cylindrical bearing or bushing 636 is preferably located between the second leg axle 644 and the inside wall of the second leg bore 642.

Referring still to FIG. 6, the second leg axle 644 includes an extension portion 650 that extends beyond an exterior surface 652 of the brake member 602. A first large pulley member 654 is positioned on the extension portion 650 of the second leg axle 644. A second large pulley member 656 is interconnected to the first large pulley member 654 using connectors 42, such as bolts or screws. Sandwiched between the first and second large pulley members 654 and 656 is a low friction track insert 660. Between an inside edge of the first large pulley member 654 and the exterior surface 652 of the brake member 602 is a biasing member, such as brake clock spring 662, the function of which will also be described below. A first end of the brake clock spring 662 is preferably interconnected to the first large pulley member 654. In addition, a second end of the brake clock spring 662 is preferably interconnected to the second leg 606 using a tethering wire or prong 664 and a connector 42. The first and second large pulley members 654 and 656, together with the track insert 660 and brake clock spring 662 and associated connectors combine to form large pulley assembly 666.

Interconnected to an extension portion 668 of the first leg axle 626 is detent spring 670. The detent spring 670 includes a detent spring leg 672 having an angled distal end portion 674. In addition, the detent spring 670 includes a second spring leg 676. When fully assembled, the angled distal end portion 674 is inserted through gap 678 in the track insert 660 and into detent 680 of the first large pulley member 654. In addition, the second spring leg 676 is preferably positioned against drum 616, an axle, or other structure operatively associated with the drum 616.

Figure 7:
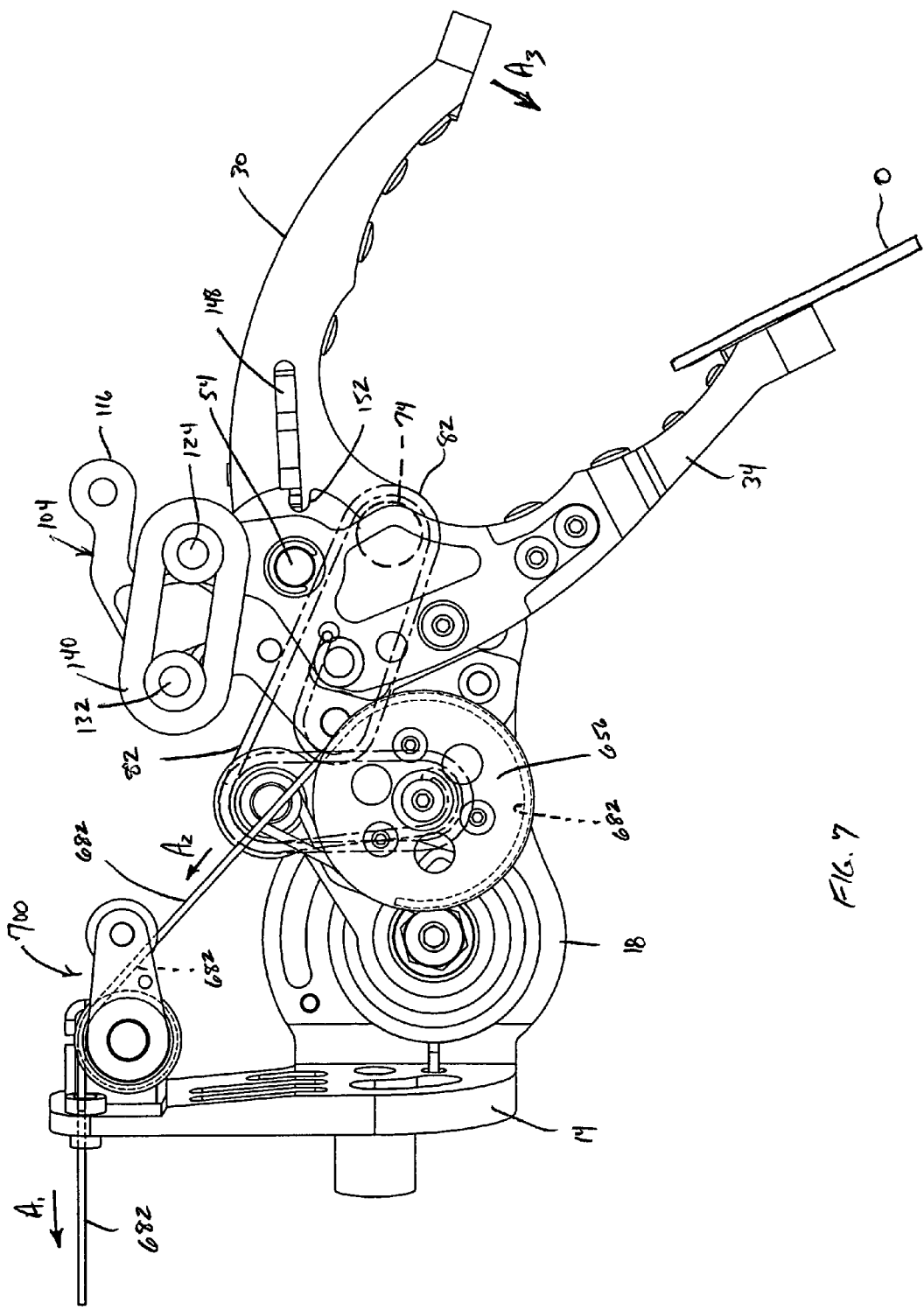
FIG. 7 is a side elevation view of the device shown in FIG. 1, with routing of the tendon shown in phantom.

Referring now to FIG. 7, prehensor 10 comprising the brake assembly 600 is depicted with an input cable 682 leading to the large pulley assembly 666. The input cable 682 preferably passes through an opening in base member 14 and passes through a guide pulley and passive holding assist clutch 700 before reaching the large pulley assembly 666. The input cable 682 is secured to the large pulley assembly 666, such as by tying or clamping the input cable 682 to the second large pulley member 656. The guide pulley and passive holding assist clutch 700 allows the tension in the input cable 682 to be reduced slightly without the brake assembly 600 rotating back. This maintains the tension in the forward portion of the prehensor 10 when the input tension in the input pulley 682 is relaxed slightly. The concept of a passive holding assist clutch is presented in U.S. Pat. No. 6,010,536, which is hereby incorporated by reference in its entirety.

FIG. 7 also shows the tendon 82 that is wrapped around the pulleys 628 and 646 of the brake assembly 600, and around the pulley 74 of the closing digit 30. Arrows A1 and A2 show the direction that the input cable 682 is pulled to create tension in the tendon 82. Arrow A3 shows the direction the closing digit 30 moves to reach object O.

Figure 9:
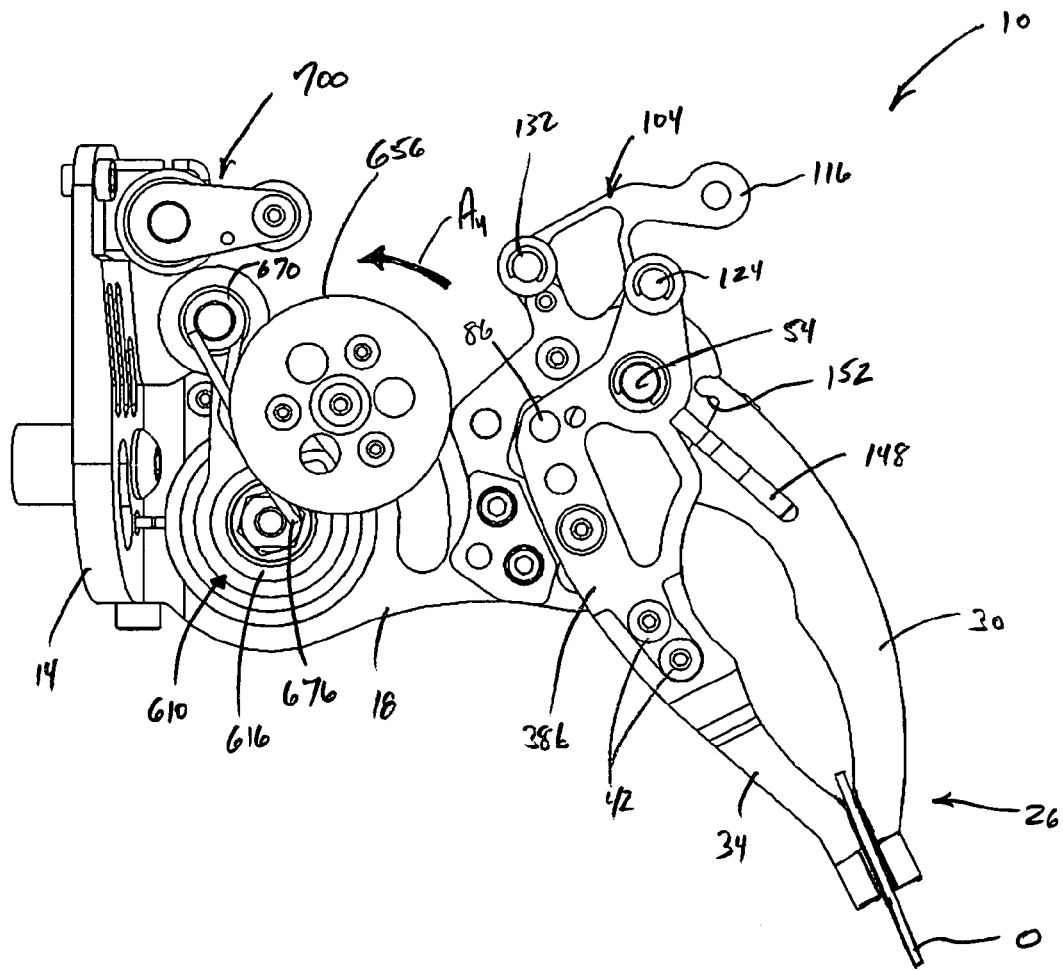
FIG. 9 is a side elevation view of the device shown in FIG. 8, where the device is in voluntary closing mode with the closing digit grasping an object.

Referring now to FIGS. 7-9, in use, the Bowden cable (not shown) is interconnected to an input cable 682, which, as noted above, is wound around the second large pulley member 656. When pulled, tension applied to the input cable 682 causes the brake member 602 to rotate around the drum 616, as shown by the direction of arrow A4 in FIG. 9. This rotation by brake member 602 transfers a tension force to tendon 82 because the tendon 82 is wound around pulleys 628 and 646 of brake member 602, and is further wound around pulley 74 of closing digit 30. The closing digit 30 is thus forced to come into contact with object O. This process is also referred to herein as "grasping" or "sizing." Detent spring 670 resists rotation of the large pulley assembly 666 and the second leg axle 644 until the sizing process is completed. Subsequently, if additional gripping forces is desired by the user, for example, the user is grasping a dog's leash as opposed to an egg, then the user continues to increase the tension in input cable 682. As input tension is increased, the object resists further sizing motion and a net pinching force appears across first leg 604 and second leg 606 of the brake member 602, thereby locking the inside surface 612 of chamber 610 in place on the drum 616. As tension in input cable 682 is increased further, the resistance of the detent spring 670 is overcome, and the angled distal end portion 674 of the detent spring leg 672 is forced out of the detent 680 of the first large pulley member 654 of the large pulley assembly 666. The angled distal end portion 674 of the detent spring leg 672 then slides along the low friction outer surface 684 of the track insert 660, and both the large pulley assembly 666 and the second leg axle 644 begin to rotate, thereby increasing the tension in the tendon 82, and therefore the grip pressure applied by the digits 26. The tendon 82 is taken up in the same way a winch draws in cable, with a mechanical advantage proportional to the ratio of the pulley and shaft diameters. Effectively, the closing digit 30 is winched down onto the object O, causing still higher pinch force to be applied. The brake member 602 remains set on the drum 616 because the pinching force acting across its legs 604 and 606 remains above the value required to set it originally. As a result, the pulling of the tendon 82 continues until 1) the desired pinch force is reached, 2) the user cannot generate more excursion, i.e. input cable 682 and tendon 82 displacement, or 3) the input cable 682 reserve length wrapped on the large pulley assembly 666 is exhausted. Thus, the brake assembly 600 takes energy it receives from the user as cable input, (i.e., force and displacement), and transforms it first into low-force/high-displacement output used to size the closing digit 30 to the object O, and further converts the energy from the input cable 682 into high-force/low-displacement output to provide large traction or gripping forces to objects squeezed by the digits 26. The delay in shifting mechanical advantage is deliberate, and ensures that the shift does not occur too soon, wasting the high-force portion of the grasp cycle in sizing or deforming compliant objects. The end result is that users can achieve high grip forces with minimal input tension and thereby avoid harness chafing, excessive axillary pressure, and unnecessary equipment wear. After the tension on the input cable 682 is released, the brake clock spring 662 rewinds the input cable 682, whereby the large pulley assembly 666 rewinds and the angled distal end portion 674 of the detent spring 670 slides back into detent 680 through gap 678 of insert 660.

The detent spring 670 of brake assembly 600, in combination with the clamping action of brake member 602 on drum 616 thus delays the transition from a first mechanical advantage of low-force/high displacement to a second higher mechanical advantage of high-force/low-displacement. The detent spring 670 not only automatically changes the mechanical advantage, but also prevents premature shifting from the first to second mechanical advantages, which prevents wasting energy when grasping compliant objects. Furthermore, the resistance of detent spring 670 can be customized for a specific user of the device, thus providing a set minimum input tension required before the angled distal end portion 674 disengages from detent 680, after which high tension forces are developed in the tendon 82.

To operate the prehensor 10 to both size and grip and object O, the user first interconnects the prehensor 10 to a prosthetic device (not shown) and also interconnects the input cable 682 to the Bowden cable (not shown) of the prosthetic and any associated harness. The user then moves the prehensor 10 such that an object O is positioned between the digits 26. The user then applies a tension force to the input cable 682 by pulling on the Bowden cable. By increasing the tension in the Bowden cable, the input cable 682 is pulled and this action causes the brake assembly 600 to rotate relative to the longitudinal member 18; however, the large pulley assembly 666 does not rotate relative to the longitudinal member 18. This is the first mechanical advantage of the prehensor 10. The rotation of the brake assembly 666 creates increasing tension in the tendon 82, which rotates the closing digit 30 on to the object O.

Subsequent to grasping the object O by sizing the closing digit 30 to the object O, the user may then continue to pull on the Bowden cable to create higher gripping pressure on the object O. During this process, the brake assembly 600 first stops rotating on drum 616 because a sufficient pinch force is applied across the first leg 604 and second leg 606 of the brake member 602 once the object O is sized. Thereafter, the second mechanical advantage is achieved when the angled distal end portion 674 of the detent spring leg 672 disengages from the detent 680 of the first large pulley member 654. When the angled distal end portion 674 disengages from the detent 680, the large pulley assembly 666 rotates relative to the brake member 602, thereby creating ever increasing tension in tendon 82, and thus higher gripping pressure at the digits 26. To release the object O, the user relaxes the tension in the Bowden cable, and the closing digit 30 returns to its starting position, as does the brake assembly 600 and large pulley assembly 666, which rewinds the input cable 682 onto the second large pulley member 656.

Brakeless VMA Assembly

As described above, a brake assembly may be used to provide a variable mechanical advantage in a prehensor. However, an alternate mechanism may be used to achieve this function. Accordingly, the following paragraphs describe a prehensor device that does not use a brake assembly, but instead utilizes a rotating biasing member to create a variable mechanical advantage in the prehensor. As with the prehensor described above that uses a brake assembly, a brakeless VMA assembly also provides a mechanism for allowing a user of the prehensor to first grasp an object and then apply a tighter gripping force. The brakeless VMA assembly converts the input cable tension into both grasping motion and tighter gripping pressure as described below.

Figure 10:
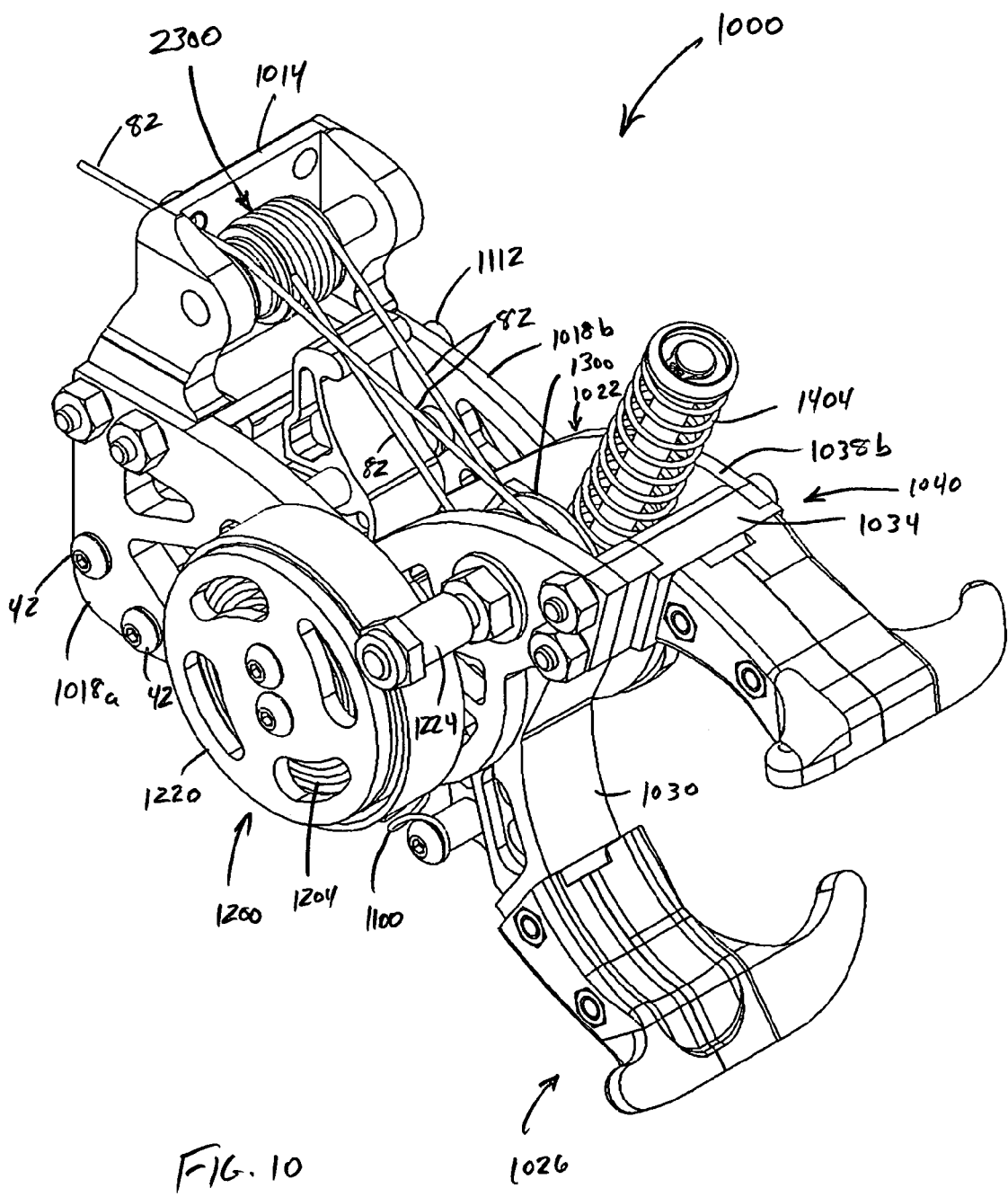
FIG. 10 is a perspective view of a brakeless device in accordance with embodiments of the present invention.
Figure 11:
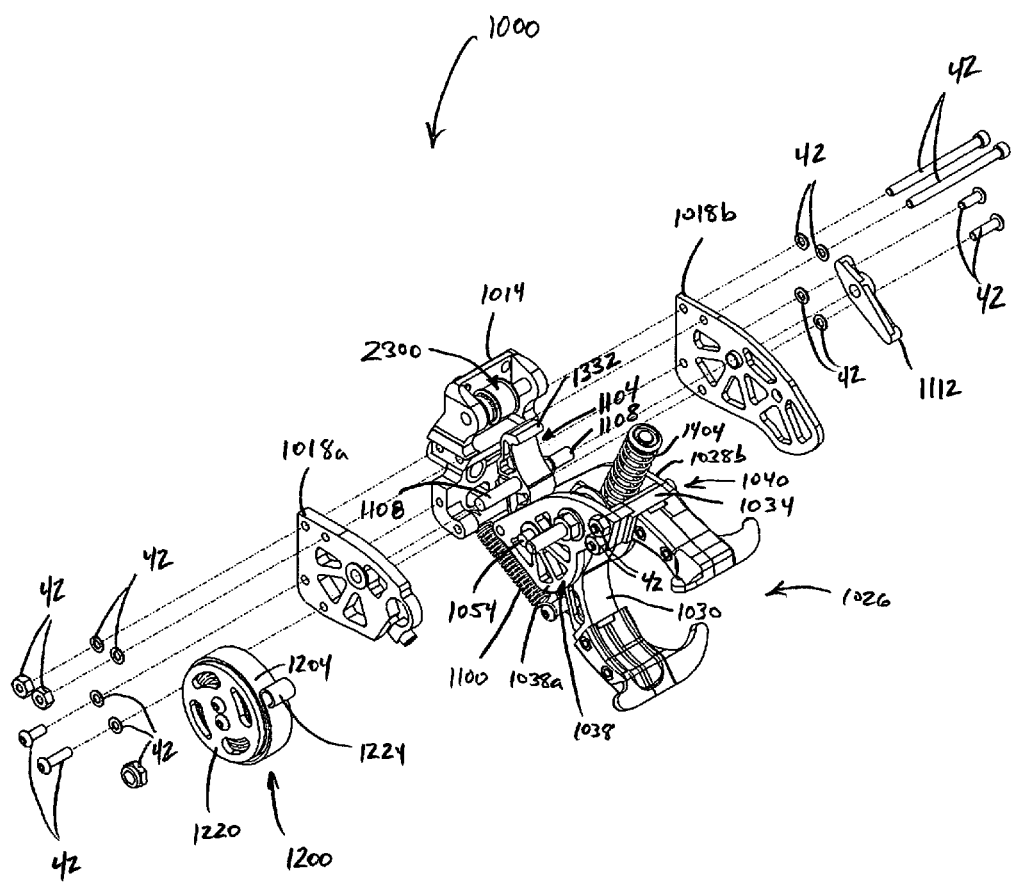
FIG. 11 is a partially exploded view of the device shown in FIG. 10.

Referring now to FIGS. 10 and 11, in accordance with embodiments of the present invention, a prehensor 1000 comprising a brakeless VMA assembly is shown. The prehensor 1000 includes a base member 1014 that serves as a mounting plate for interconnecting the prehensor 1000 to a prosthetic attachment or harness device (not shown) operatively associated with a portion of the body of the user, such as the user's arm. Alternatively, the prehensor 1000 may be interconnected to a robot or robotic device. Interconnected to the base member 1014 is at least one longitudinal member. For the embodiment depicted in FIGS. 10-17, the prehensor 1000 preferably includes two longitudinal members 1018a and 1018b, although alternate configurations are possible and are within the scope of the invention. Base member 1014 and longitudinal members 1018a and 1018b are shown interconnected using connectors 42; however, base member 1014 and longitudinal members 1018a and 1018b may be constructed of one piece.

The longitudinal members 1018a and 1018b include a distal region 1022 that is interconnected to the digits 1026 of the prehensor 1000. The digits 1026 preferably include a closing digit 1030 and an opening digit 1034. For the embodiment shown in FIGS. 10-17, the opening digit 1034 preferably includes an opening digit forked portion 1038 at the rear portion 1040 of the opening digit 1034. The opening digit forked portion 1038 is configured for interconnecting rear portion 1040 of the opening digit 1034 to the distal region 1022 of the longitudinal members 1018a and 1018b. The opening digit forked portion 1038 may comprise a plurality of pieces. For example, as shown in FIG. 13, in one embodiment the opening digit forked portion 1038 includes a first opening digit forked member 1038a and a second opening digit forked member 1038b, where upon assembly, the second opening digit forked member 1038b is interconnected to the first opening digit forked member 1038a using one or more connectors 42, such as bolts or screws. Alternatively, the open digit 1034 and open digit forked members 1038a and 1038b may be constructed of a single piece, as opposed to the plurality of pieces shown in FIG. 13.

For the embodiment shown in FIGS. 10-17, the opening digit forked members 1038a and 1038b are situated to the interior of the longitudinal members 1018a and 1018b. Positioned within the opening digit forked members 1038a and 1038b resides the closing digit rear portion 1050 of the closing digit 1030.

Common axle 1054 passes through opening digit bore 1058 of the opening digit forked members 1038a and 1038b, through longitudinal member bore 62 of the longitudinal member 1018b, and through the closing digit bore 1066 of the closing digit rear portion 1050. When rotated, such as by opening or closing the digits 1030 and 1034 of the prehensor 1000, both the closing digit 1030 and the opening digit 1034 pivot about the common axle 1054.

Figure 12:
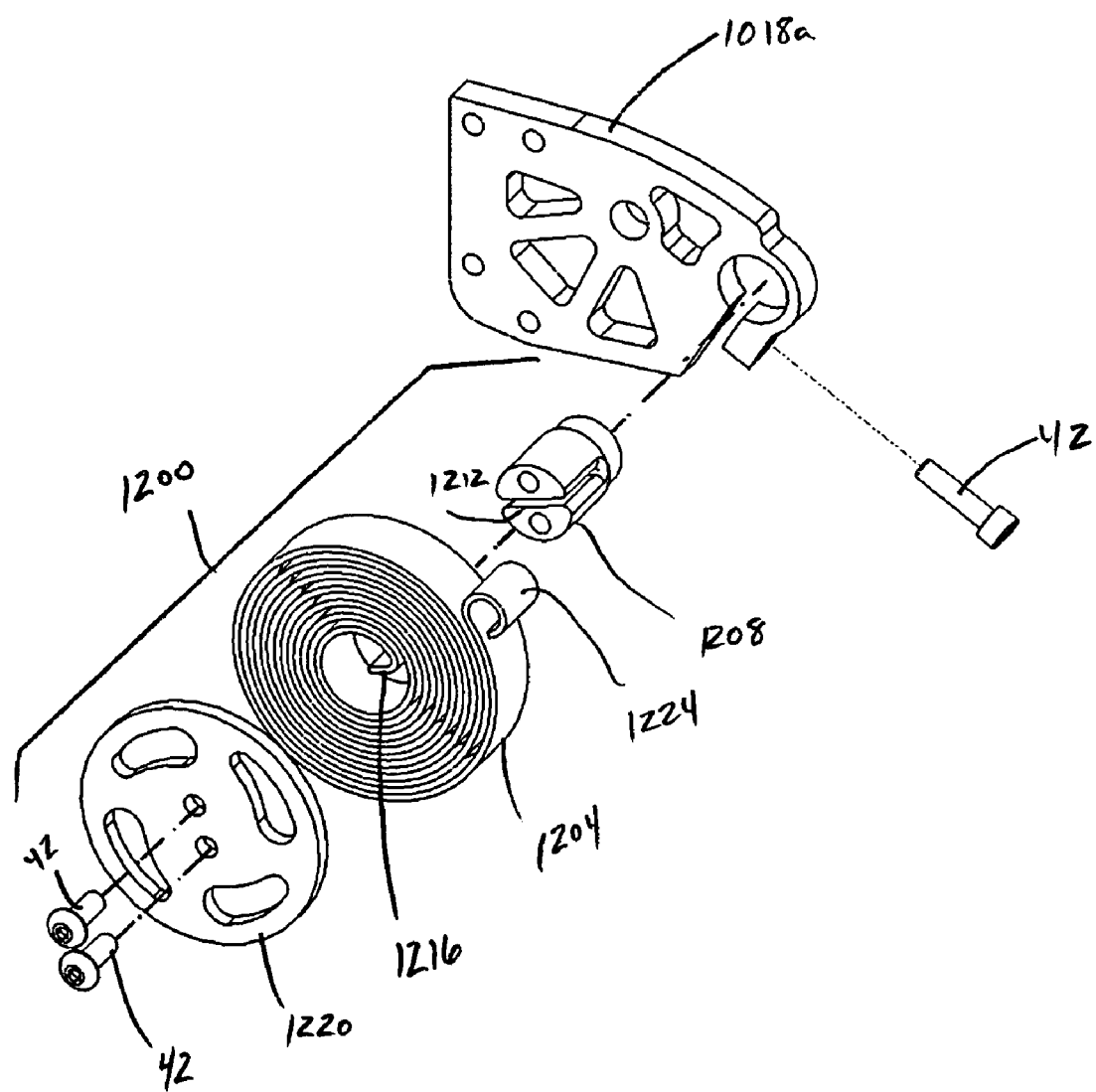
FIG. 12 is an exploded view of the opening digit biasing assembly associated with the device shown in FIG. 10.
Figure 13:
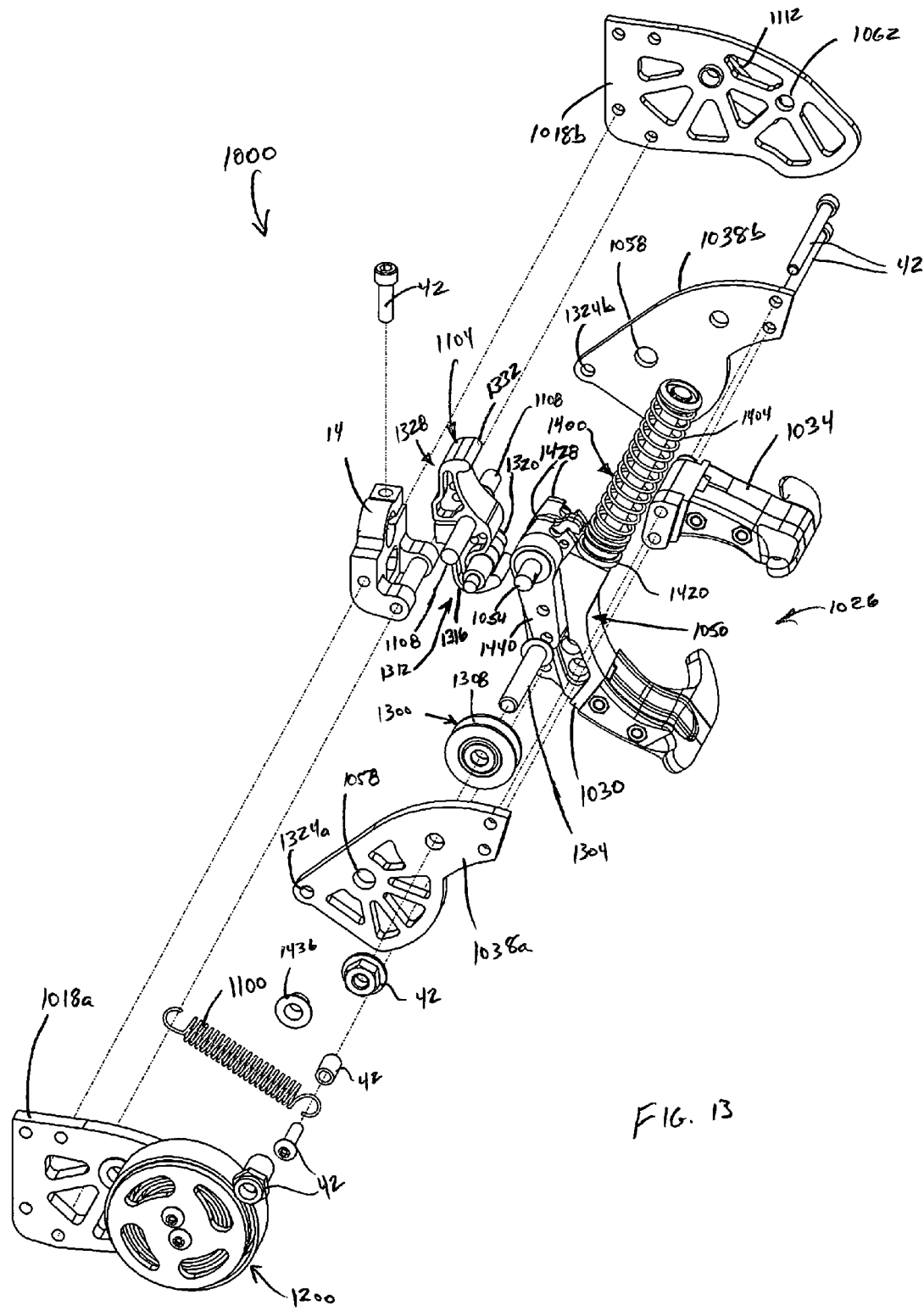
FIG. 13 is another partially exploded view of the device shown in FIG. 10.

Referring to FIG. 12, in accordance with embodiments of the present invention, the prehensor 1000 may include an opening digit biasing assembly 1200, the function of which will be discussed below. The opening digit biasing assembly 1200 preferably comprises a biasing member, such as a clock spring 1204. The clock spring 1204 is interconnected to longitudinal member 1018a using a center member 1208 that is clamped to the longitudinal member 1018a using connector 42. The center member 1208 includes a center slot 1212 for receiving a center end portion 1216 of the clock spring 1204. Prior to fixing the center member 1208 to the longitudinal member 1018a, the resistance of the clock spring 1204 can be adjusted by rotating the central member 1208 after inserting the center end portion 1216 into center slot 1212 of the center member 1208. After the desired resistance is reached, the resistance is substantially locked-in by clamping or otherwise securing the rotated center member 1208 to the longitudinal member 1018a. Connectors 42 are used to interconnect a covering plate 1220 to the center member 1208. As shown in FIG. 1, an exterior end 1224 of clock spring 1204 is interconnected to opening digit forked member 1038a using a connector 42.

Figure 14:
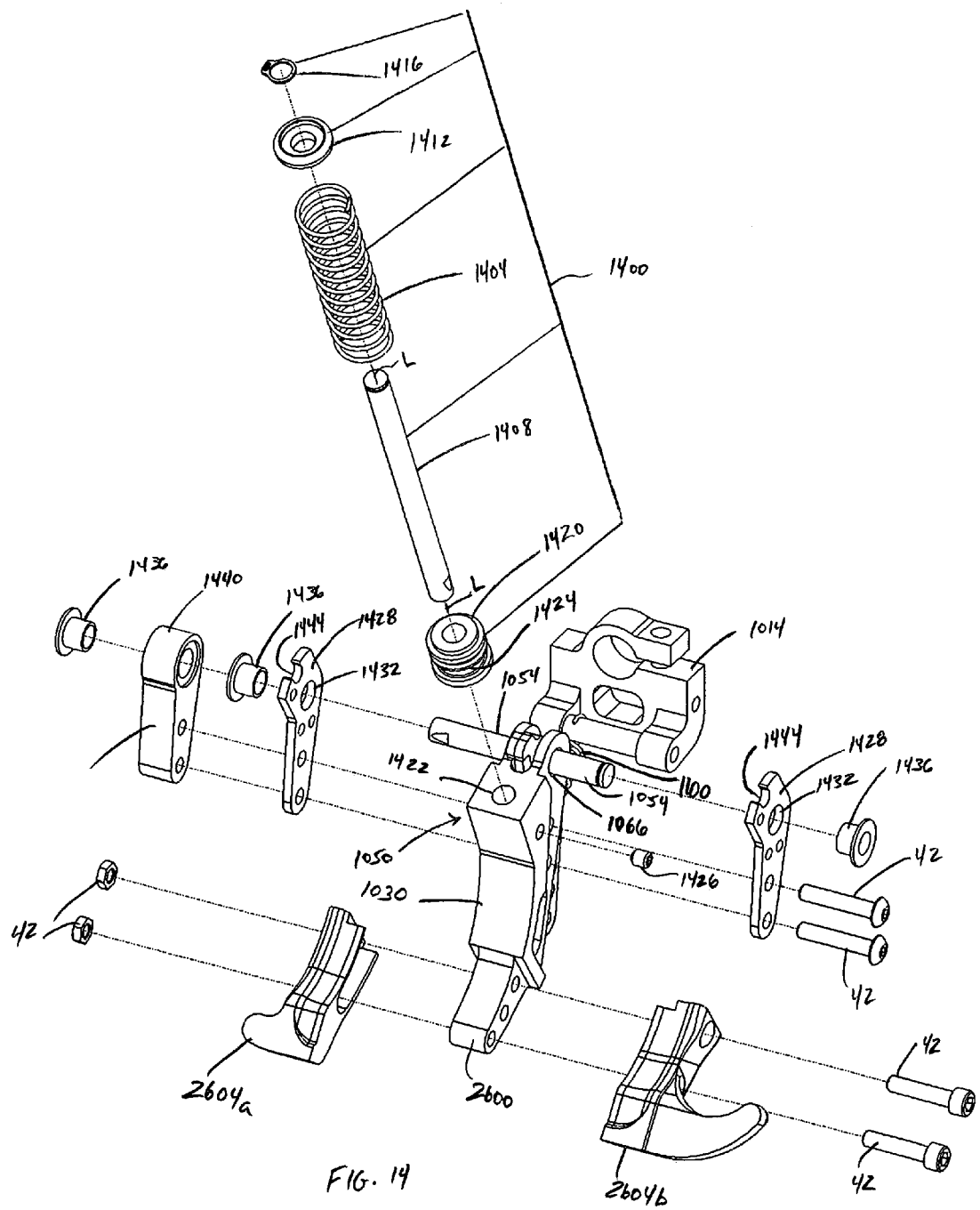
FIG. 14 is an exploded view of portions of the device shown in FIG. 10.

Referring now to FIG. 14, in accordance with embodiments of the invention, a VMA biasing assembly 1400 is preferably interconnected to the rear portion 1050 of closing digit 1030. As shown in FIG. 14, in one embodiment the VMA biasing assembly 1400 preferably includes a VMA spring 1404, such as a compression coil spring. The VMA spring 1404 is located over a VMA spring rod 1408. Alternative structure to the VMA spring 1404 may include a resilient plastic or rubber washer. The VMA spring 1404 is maintained on the VMA spring rod 1408 using a washer 1412 and a clip ring 1416, although other means may be used. The VMA biasing assembly 1400 also preferably includes a VMA bushing 1420 that is slidable along a longitudinal axis L-L of the VMA spring rod 1408. The VMA bushing 1420 includes a means for attaching tendon 82 to the VMA bushing 1420, such as by tying the tendon 82 around tendon slot 1424, clamping the tendon 82 to the VMA bushing 1420, or passing the tendon through an eyelet in the VMA bushing 1420. The VMA biasing assembly is interconnected to the rear portion 1050 of the closing digit 1030, such as by inserting the VMA spring rod 1408 into an opening 1422 in the closing digit 1030 and locking the VMA spring rod in place, such as by advancing a set screw 1426. In use, a user typically interconnects a harness (not shown) having a Bowden cable (not shown) to the prehensor 1000. The Bowden cable is then interconnected to a tendon 82 of prehensor 1000 to move one or more of the digits 1026. In accordance with embodiments of the present invention, the tendon 82 of the prehensor 1000 is preferably directly connected to the Bowden cable, and a separate input cable is not needed.

Referring still to FIG. 14, in accordance with embodiments of the invention, the rear portion 1050 of the closing digit 1030 also includes a closing digit side plate 1428. For the embodiment shown in FIG. 14, two closing digit side plates 1428 are provided, each closing digit side plate 1428 having a closing digit side plate bore 1432 for receiving the common axle 1054. Bushings 1436 may be used for smoother rotation of the closing digit side plates 1428 about the common axle 1054. In addition, a spacer 1440 may also be interconnected to a side portion of the rear portion 1050 of the closing digit 1030. The function of the closing digit side plates 1428 and the spacer 1440 will be described below.

Referring again to FIGS. 11 and 14, in accordance with embodiments of the present invention, the rear portion 1050 is interconnected to the base member 1014 by a closing digit return member, such as a closing digit return spring 1100. The closing digit return spring 1100 may comprise a variety of structures, such as an extension coil spring or an elastic cord. The closing digit return spring 1100 serves to return the closing digit to an open position after the grasping function is completed.

Referring again to FIG. 13, in accordance with embodiments of the present invention, the prehensor 1000 includes a rotatable opening digit pulley 1300 that is interconnected to an opening digit pulley axle 1304. The opening digit pulley 1300 includes a tendon slot 1308 for receiving a wrapping of the tendon 82.

Still referring to FIGS. 11 and 13, in accordance with embodiments of the present invention, the prehensor 1000 includes a selectably rotatable latch 1104 for designating a voluntary opening of voluntary closing mode, as will be described below. The latch 1104 preferably includes pivoting axle 1108 about which the latch 1104 rotates. The pivoting axle 1108 is rotatably interconnected to longitudinal members 1018a and 1018b. In addition, a mechanism for toggling the latch 1104 is preferably provided at an accessible position. In accordance with one preferred embodiment, and as best seen in FIG. 11, the mechanism for toggling the latch 1104 comprises a latch handle 1112 located proximate the longitudinal member 1018b.

Referring now to FIG. 13, the latch 1104 preferably includes a latch first end 1312 that comprises a mechanism for locking the opening digit 1034. In one preferred embodiment, the latch first end 1312 includes a first end angled portion 1316 that engages an opening digit lock axle 1320. More particularly, as best seen in FIG. 15, the latch first end 1312 includes a pocket region 1318 for receiving the opening digit lock axle 1320 and preventing rotation of the opening digit 1034, thereby allowing the tendon 82 to pull the VMA bushing 1420, resulting in rotation of the closing digit 1030. The opening digit lock axle 1320 is interconnected to first opening digit forked member 1038a and second opening digit forked member 1038b at lock axle bores 1324a and 1324b, respectively. It is to be understood that a variety of means for locking the opening digit 1034 are contemplated, including a friction fit and a separate engagable device, such as an insertable mechanism such as a pin.

Referring still to FIG. 13, the latch 1104 preferably includes a latch second end 1328 that comprises a mechanism for locking the closing digit 1030. In one preferred embodiment, the latch second end 1328 includes a second end angled portion 1332 that engages an indentation 1444 in at least one of the closing digit side plates 1428. Upon engaging the indentation 1444, the latch 1104 prevents the closing digit from rotating, and allows the tendon 82 to pull the opening digit pulley 1300, thereby rotating the opening digit 1034. It is to be understood that a variety of means for locking the closing digit 1030 are contemplated, including a friction fit and a separate engagable device such as an insertable pin.

It is noted that the rotatable latch 1104 is not necessary if a prehensor is constructed to function in only one of either a voluntary opening or voluntary closing mode. For a prehensor operable in voluntary closing mode only, including operating with a variable mechanical advantage, the latch 1104 may be fixed in its first position, wherein it locks the opening digit 1034 from rotating, thereby allowing the tendon 82 to pull the VMA bushing 1420, resulting in rotation of the closing digit 1030. Alternatively, if a prehensor is desired for manufacture to operate in a voluntary opening mode only, then the latch 1104 may be fixed in its second position, wherein it locks the closing digit 1030 from rotating and allows the tendon 82 to pull the opening digit pulley 1300, thereby rotating the opening digit 1034.

Referring now to FIG. 15, a side elevation view of prehensor 1000 is shown, with a number of structures omitted for clarity. FIG. 15 depicts the position of the latch 1104 when the prehensor is in a voluntary closing mode. As noted earlier, the opening digit 1034 is locked and prevented from moving by latch 1104, and although the tendon 82 passes around opening digit pulley 1300, since the opening digit 1034 is locked, the opening digit 1034 does not move. It is noted that for a prehensor with only a voluntary closing mode of operation, the opening digit pulley 1300 may be omitted.

Referring now to FIGS. 15-15B, as noted above, the tendon 82 is tied to an eyelet or otherwise is interconnected to VMA bushing 1420, such as by being wrapped and tied around bushing slot 1424. As shown in FIG. 15A, the bushing 1420 also preferably includes a bushing flange 1500 for receiving a bushing catch 1504 of closing digit lock 1508. The closing digit lock 1508 is rotatably positioned on common axle 1054. When the latch 1104 in the a first position locking the opening digit 1034, the closing digit lock 1508 is biased in an unlocked position by closing digit lock spring 1512. In the voluntary closing mode, the prehensor 1000 shown in FIGS. 15-15B provides a variable mechanical advantage as will now be described.

Referring still to FIG. 15, the prehensor 1000 can be used to grasp an object O with an automatic variable mechanical advantage. The configuration of prehensor 1000 changes its forward force ratio in response to applied loads continuously and smoothly. Prior to applying any tension to the Bowden cable interconnected to tendon 82, the closing digit 1030 is in its fully open position, as depicted in FIG. 15. The closing digit return spring 1100 ensures the closing digit 1030 returns to its fully open position when input cable tension P vanishes.

The pinch force F that can be generated at the digit tips is calculated using basic lever laws:

$$F = P(L_1/R) \qquad \text{Equation \{3\}}$$

Where $L_1$ is the starting lever arm length, and R is the effective length of the closing digit 1030 and remains constant.

Alternatively, a forward force ratio (FFR) may be defined as:

$$FFR_{min} = (L_1/R) \qquad \text{Equation \{4\}}$$

For the embodiment shown as prehensor 1000, the VMA spring 1404 has a sufficient spring constant to provide a bias force that keeps the VMA bushing 1420 in its initial position. This ensures that the initial lever $L_1$ remains at its starting (lowest) value, thereby setting the FFR at its smallest value according to Equation {4} above. The position of the VMA spring rod 1408 and orientation of tendon 82 leading to the VMA bushing 1420 are preferably configured to ensure that arc angle α remains at or less than 90° for the full range of motion.

Figure 16:
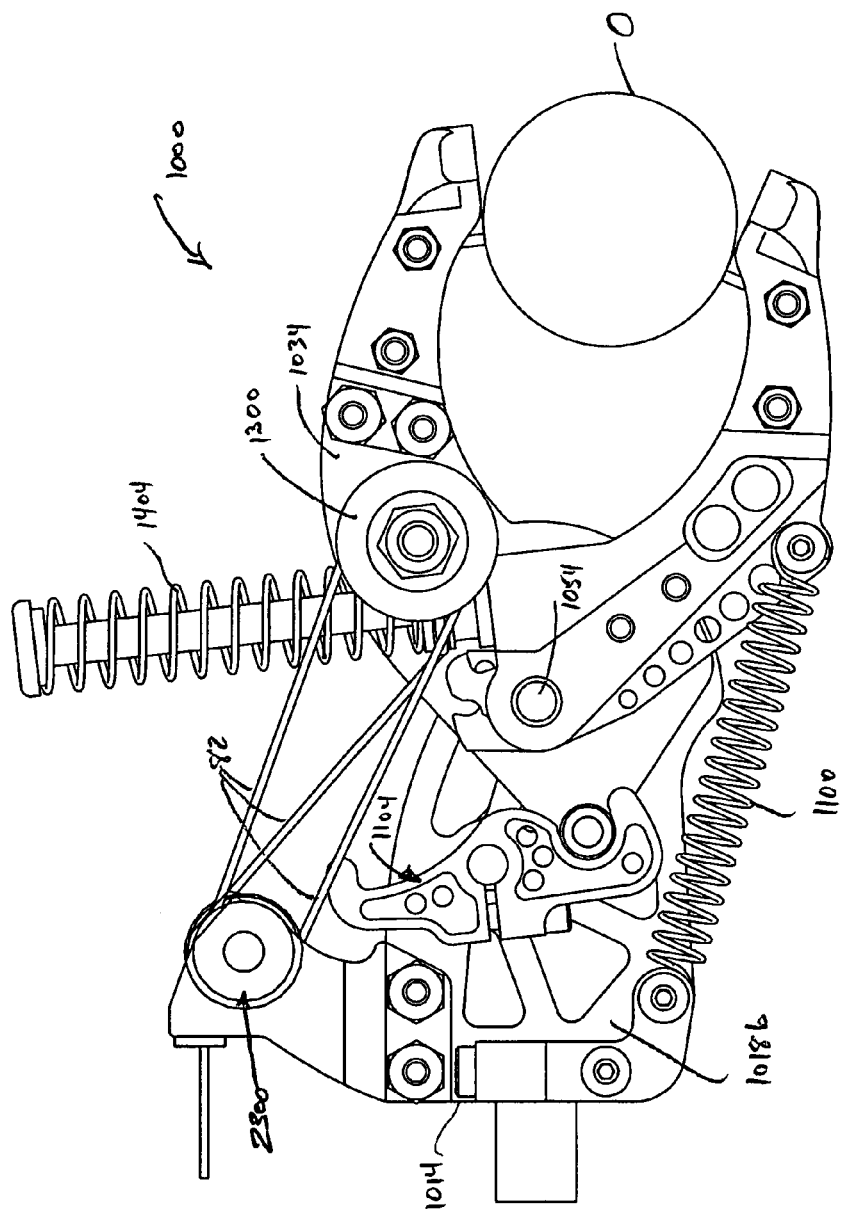
FIG. 16 is another side elevation view of the device shown in FIG. 15, wherein the device is in voluntary closing mode with the closing digit grasping the object.
Figure 17:
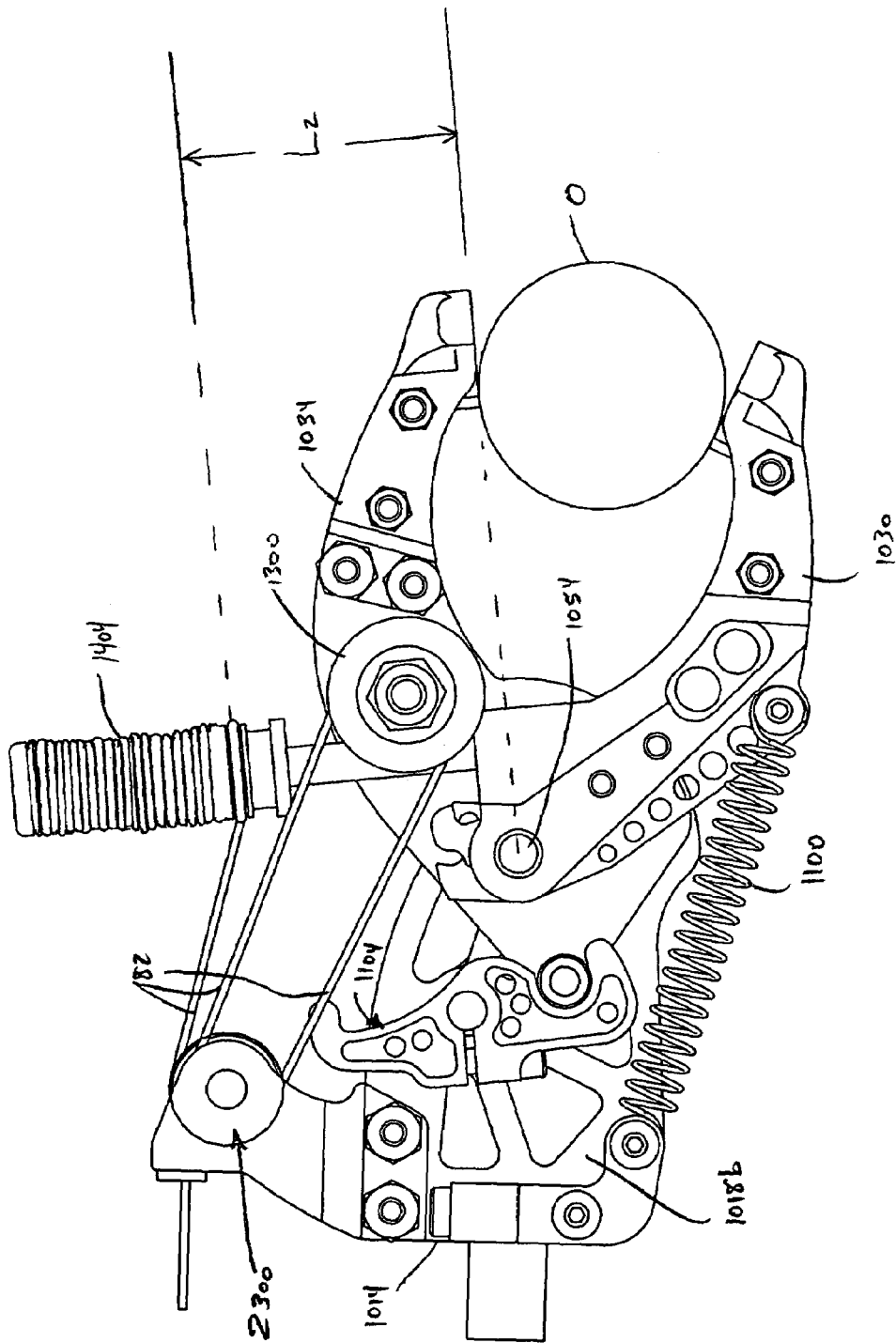
FIG. 17 is another side elevation view of the device shown in FIG. 15, wherein the device is in voluntary closing mode with the closing digit applying a gripping pressure to the object.

Referring now to FIG. 16, as input force P increases, the closing digit 1030 begins to rotate counter-clockwise until object O is encountered. The VMA spring 1404 and the closing digit return spring 1100 are each sized to permit the closing digit 1030 to be rotated fully counter-clockwise against an intervening item such as object O, or even the opposing opening digit 1034 without the VMA spring 1404 being compressed. However, when object O is encountered, as depicted in FIG. 16, the closing digit 1030 movement is arrested and motion halts (unless the object O is compressible). Referring now to FIG. 17, as the user then continues to increase the tension P in tendon 83, two things occur: (1) a component of the tension in tendon 82 acts to slide VMA bushing 1420 along the VMA spring rod 1408 causing the VMA spring 1404 to be compressed; and (2) as the VMA bushing 1420 moves radially outward along VMA spring rod 1408, its effective lever length increases causing the FFR to also increase, and thereby the force applied by the tip of the closing digit 1030 to an object being grasped. If the VMA spring 1404 is fully compressed, the effective input lever reaches a maximum length of $L_2$ driving the FFR to its highest value:

$$FFR_{max}=(L_2/R) \qquad \text{Equation \{5\}}$$

Thus, the VMA biasing assembly 1400 takes energy it receives from the user as cable input, (i.e., force and displacement), and transform it first into low-force/high-displacement output used to size the closing digit 1030 to the object O, and further converts the energy from the tendon 82 into high-force/low-displacement output to provide large traction or gripping forces to objects squeezed by the digits 1026.

To operate the prehensor 1000, after making the appropriate connections of the prehensor 1000 to any prosthetic and/or harness, the user then moves the prehensor 1000 such that an object O is positioned between the digits 1026. The user then applies a tension force to the tendon 82 by pulling on the Bowden cable. By increasing the tension in the Bowden cable, the tendon 82 is pulled and this action causes the tendon 82 to rotate the VMA spring rod 1408. This is the first mechanical advantage of the prehensor 1000. The rotation of the VMA spring rod 1408 correspondingly rotates the closing digit 1030 onto the object O.

Subsequent to grasping the object O by sizing the closing digit 1030 to the object O, the user may then continue to pull on the Bowden cable to create higher gripping pressure on the object O. During this process, VMA spring rod 1408 substantially ceases rotating, and the VMA bushing 1420 begins to compress the VMA spring 1404. Thus, the second mechanical advantage is achieved when with the development of ever higher gripping pressure at the digits 1026. To release the object O, the user relaxes the tension in the Bowden cable, and the closing digit 1030 then returns to its starting position because of the tension applied by return spring 1100.

Figure 18:
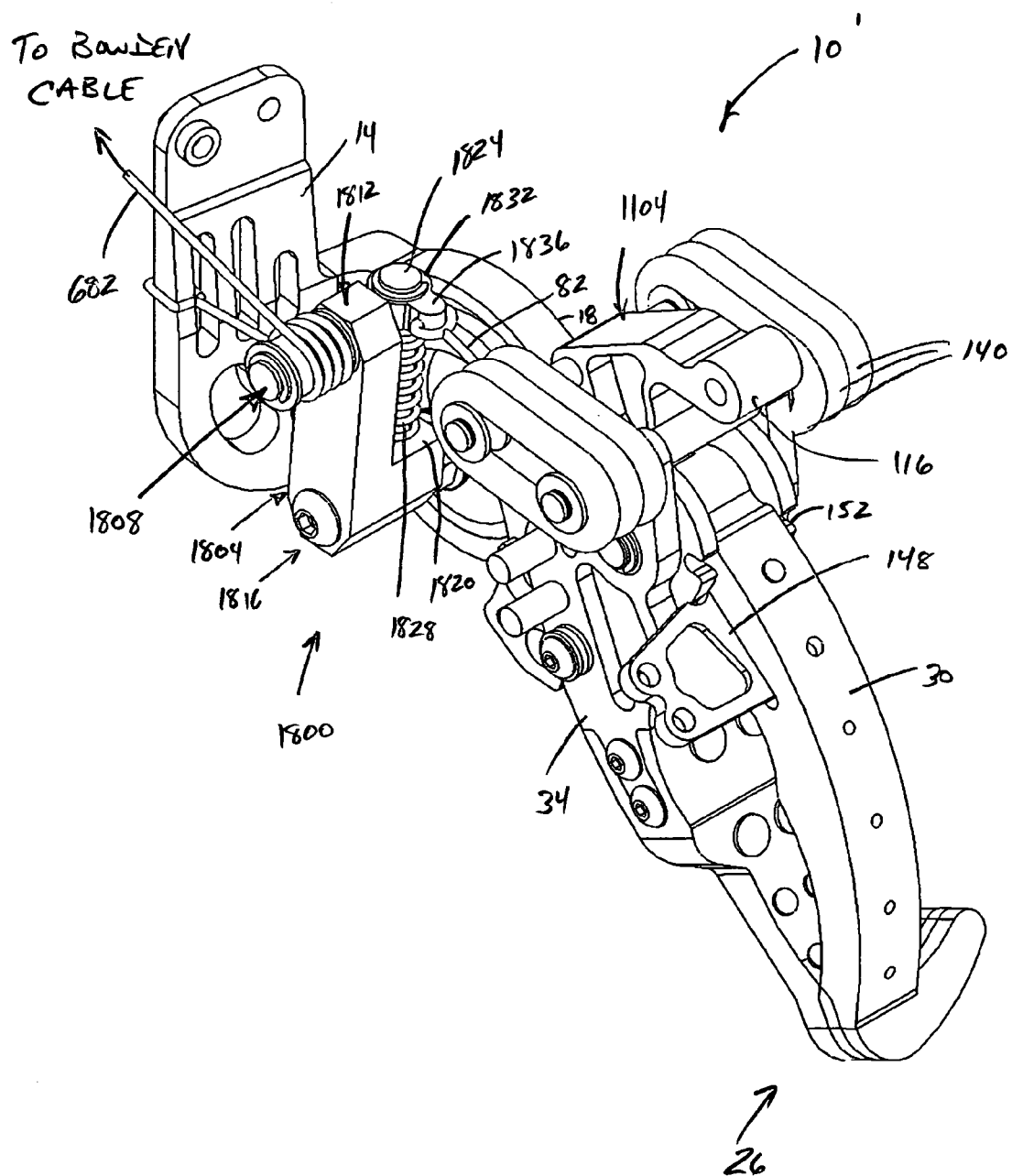
FIG. 18 is a perspective view of another brakeless device in accordance with embodiments of the present invention.
Figure 18A:
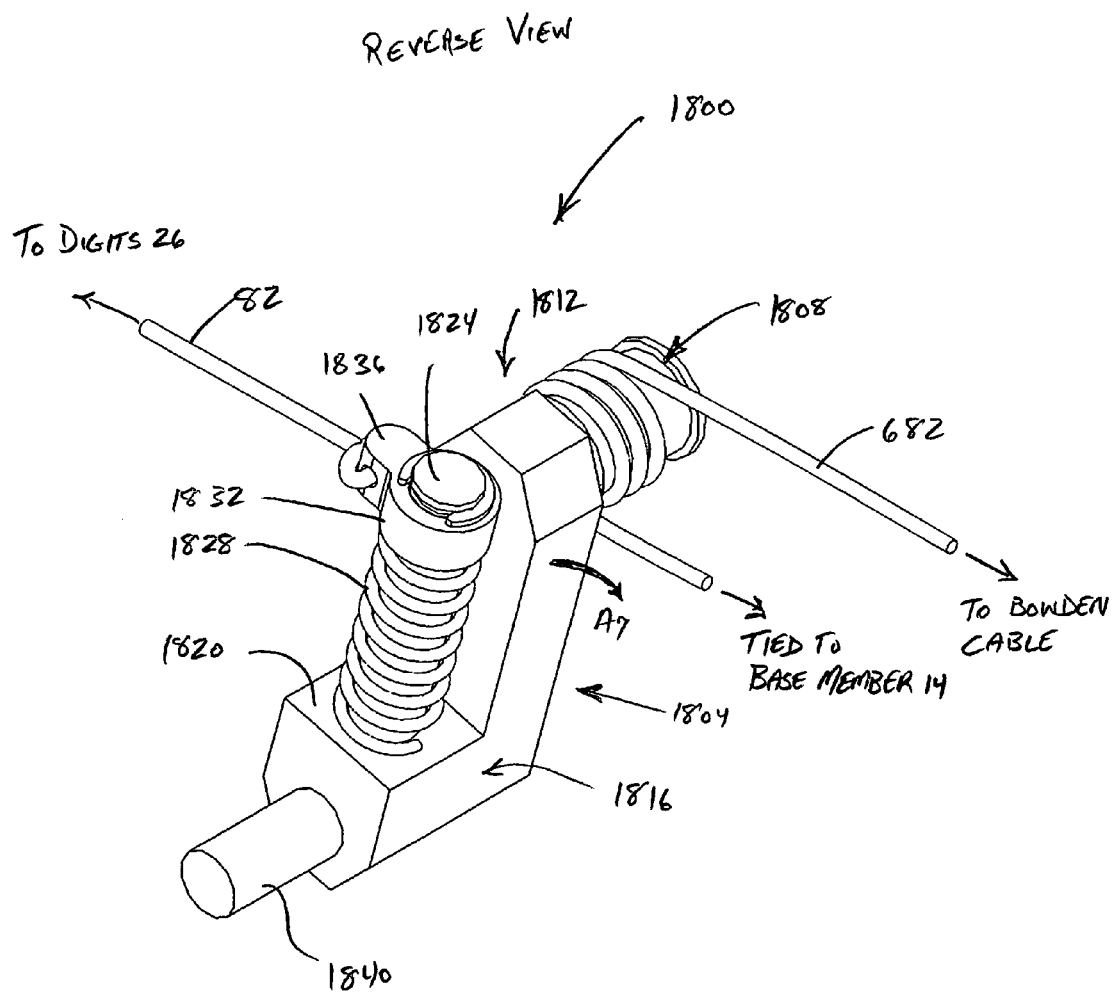
FIG. 18A is a detail reverse perspective view of components of the device shown in FIG. 18, with the VMA block assembly corresponding to the digits in a grasping state.
Figure 18B:
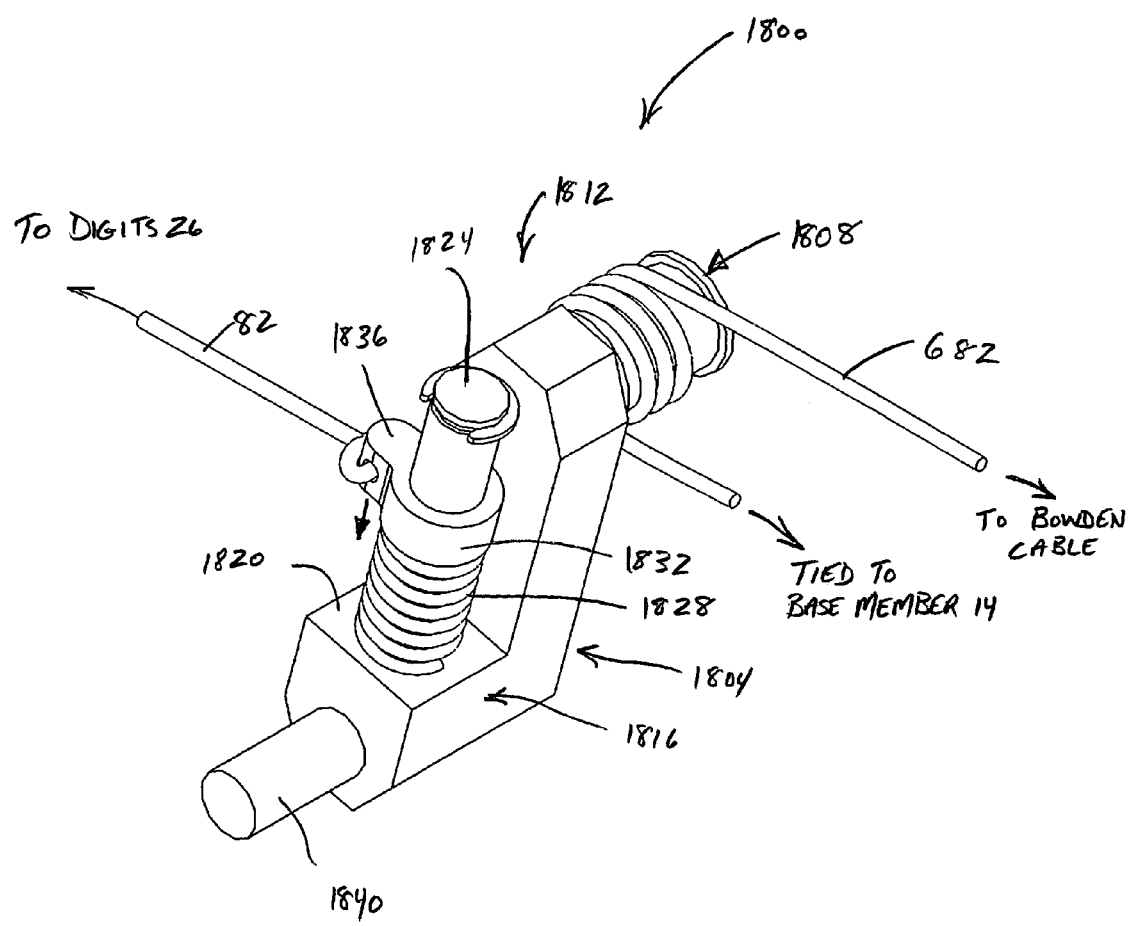
FIG. 18B is the same detail reverse perspective view of the components shown in FIG. 18A, with the VMA block assembly corresponding to the digits in a gripping state.

Referring now to FIGS. 18-18B, a separate embodiment of a brakeless VMA assembly is described. The prehensor 10' replaces the brake assembly 600 of prehensor 10 with a rotatable VMA block assembly 1800. The VMA block assembly 1800 comprises a rotatable block 1804 including a passive holding assist clutch 1808 interconnected to a first end 1812 of block 1804. The VMA block assembly 1800 further includes a second end 1816 that includes a block base surface 1820 having a block rod member 1824 interconnected to the base surface 1820. The block rod member 1824 holds a block biasing member, such as block coil spring 1828. A tendon collar 1832 is slidably interconnected to the block rod member 1824 such that it can travel up and down the block rod member 1824 while compressing and releasing block coil spring 1828. The tendon collar 1832 preferably includes a means for attaching the tendon 82 to the tendon collar 1832, such as an eyelet 1836. The second end 1816 of the block 1804 further comprises a rotatable block axle 1840 for interconnecting the block 1804 to the longitudinal member 18 of the prehensor 10'.

Referring now to FIGS. 18A and 18B, the VMA block assembly 1800 is shown during sizing and gripping, respectively. During the sizing process, the tension in the input cable 682 rotates the block 1804 in the direction of arrow A7 and thus the closing digit 30 until the closing digit contacts the object. After contacting the object, the second mechanical advantage component engages, wherein the block 1804 substantially ceases rotating and, as shown in FIG. 18B, the tendon collar 1832 travels along the block rod member 1824, thereby compressing the block coil spring 1828 and developing gripping pressures on the object.

Thus, the VMA block assembly 1800 takes energy it receives from the user as cable input, (i.e., force and displacement), and transform it first into low-force/high-displacement output used to size the closing digit 30 to the object O, and further converts the energy from the input cable 682 into high-force/low-displacement output to provide large traction or gripping forces to objects squeezed by the digits 26.

To operate the prehensor 10', after making the appropriate connections of the prehensor 10' to any prosthetic and/or harness, the user then moves the prehensor 10' such that an object O is positioned between the digits 26. The user then applies a tension force to the input cable 682 by pulling on the Bowden cable. By increasing the tension in the Bowden cable, the input cable 682 is pulled and this action causes the block 1804 of the VMA block assembly 1800 to rotate. This is the first mechanical advantage of the prehensor 10'. The rotation of the block 1804 correspondingly creates a tension in tendon 82 that rotates the closing digit 30 onto the object O.

Subsequent to grasping the object O by sizing the closing digit 30 to the object O, the user may then continue to pull on the Bowden cable to create higher gripping pressure on the object O. During this process, block 1804 substantially ceases rotating, and the tendon collar 1832 begins to compress the block coil spring 1828. Thus, the second mechanical advantage is achieved when with the development of ever higher gripping pressure at the digits 26. To release the object O, the user relaxes the tension in the Bowden cable and thus the tension in the input cable 682, at which time the block coil spring 1828 releases, and the block 1804 rotates back. In addition, the closing digit 30 then returns to its starting position because of force applied to the closing digit 30 due to the closing digit return spring 68.

Selectable Voluntary Opening/Voluntary Closing Assembly

Referring again to FIGS. 1-5A, in accordance with embodiments of the present invention, the prehensor 10 may include a selectable voluntary opening/voluntary closing ("VO/VC") assembly 100. The VO/VC assembly 100 allows the user to easily switch between a voluntary opening ("VO") mode and a voluntary closing ("VC") mode using the same prehensor.

As shown in FIGS. 5 and 5A, in accordance with embodiments of the present invention, the VO/VC assembly 100 includes a rotatable cam switch 104 that can be moved from a first position for VC mode, to a second position for VO mode. The cam switch 104 is pivotably mounted to longitudinal member forked portion 46 such as by cam axle 108 that may rotate within axle openings 112 in the longitudinal member forked portion 46. The cam switch 104 includes a cam lever arm portion 116 for providing easier rotation of the cam switch 104. At the rear of the cam lever arm portion 116 resides a cam pocket 120 for receiving a first tensioning rod 124. The first tensioning rod 124 extends through first tensioning rod openings 128 in the rear portion 40 of the opening digit 30. A second tension rod 132 passes through the rear of the cam switch 104 and second tensioning rod opening 136. As discussed below, one or more elastic bands 140 may be positioned on the ends of the first and second tensioning rods 124 and 132 to create tension between the rods 124 and 132. Band retainers 144 may be used to provided a slotted receptacle for each band 140.

The VO/VC assembly 100 also preferably includes a means of locking the closing digit 30 when the prehensor 10 is being operated in the VO mode. More particularly, a closing digit locking tab 148 is located on the rear portion 50 of the closing digit 30. The closing digit locking tab 148 is movable from an unlocked position to a locked position.

To lock the closing digit 30, the closing digit locking tab 148 is aligned and at least partially inserted within at least one locking tab receptacle 152 in the longitudinal member forked portion 46.

The locking tab receptacle 152 is preferably positioned along the longitudinal member forked portion 46 such that the tendon 82 and input cable 682 are adjusted in the VO mode to set an end connector (not shown) between the Bowden cable and the input cable 682 in the same position as it exists in the VC mode. Thus, the user does not need to adjust the position of the harness and Bowden cable to switch between VC and VO modes.

Referring now to FIG. 8, the prehensor 10 is shown in the VC mode. Accordingly, the cam switch 104 is in its first position. In this position, the opening digit 34 is locked because the first tensioning rod 124 that passes though the opening digit 34 is substantially within the pocket 120 of the cam switch 104. Thus in this position, the closing digit 30 can open and close, but the opening digit 34 cannot move. FIG. 9 shows the closing digit 30 closed on object O.

Figure 19:
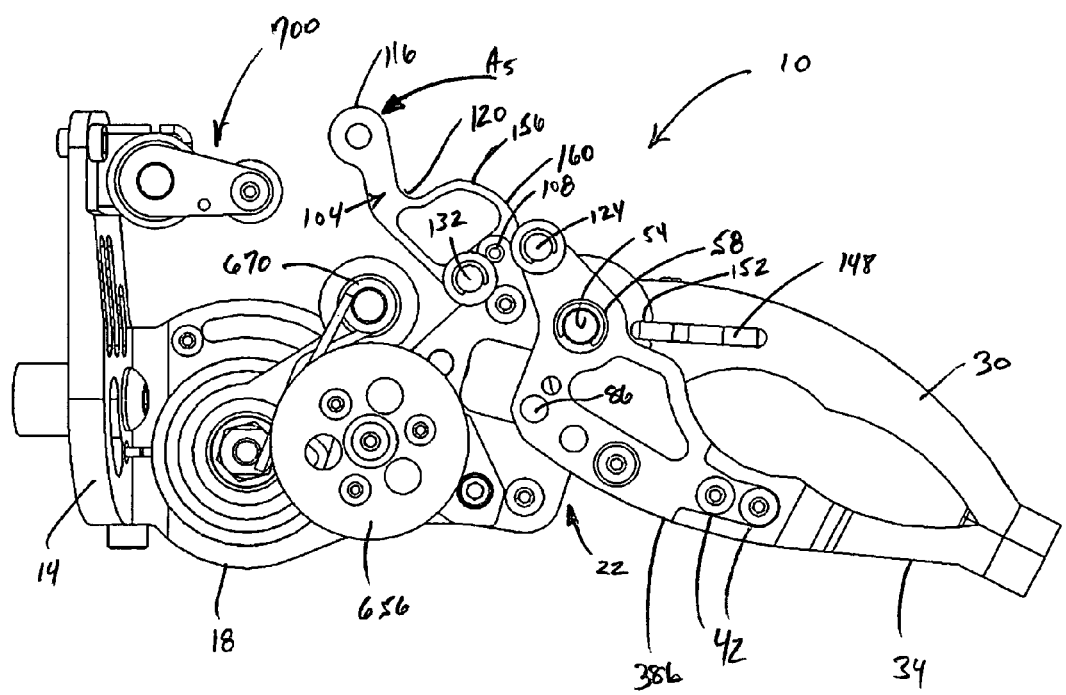
FIG. 19 is a side elevation view of the device shown in FIG. 1, excluding the input cable and tendon for clarity, wherein the device is in voluntary opening mode with the opening digit fully closed against the closing digit.
Figure 20:
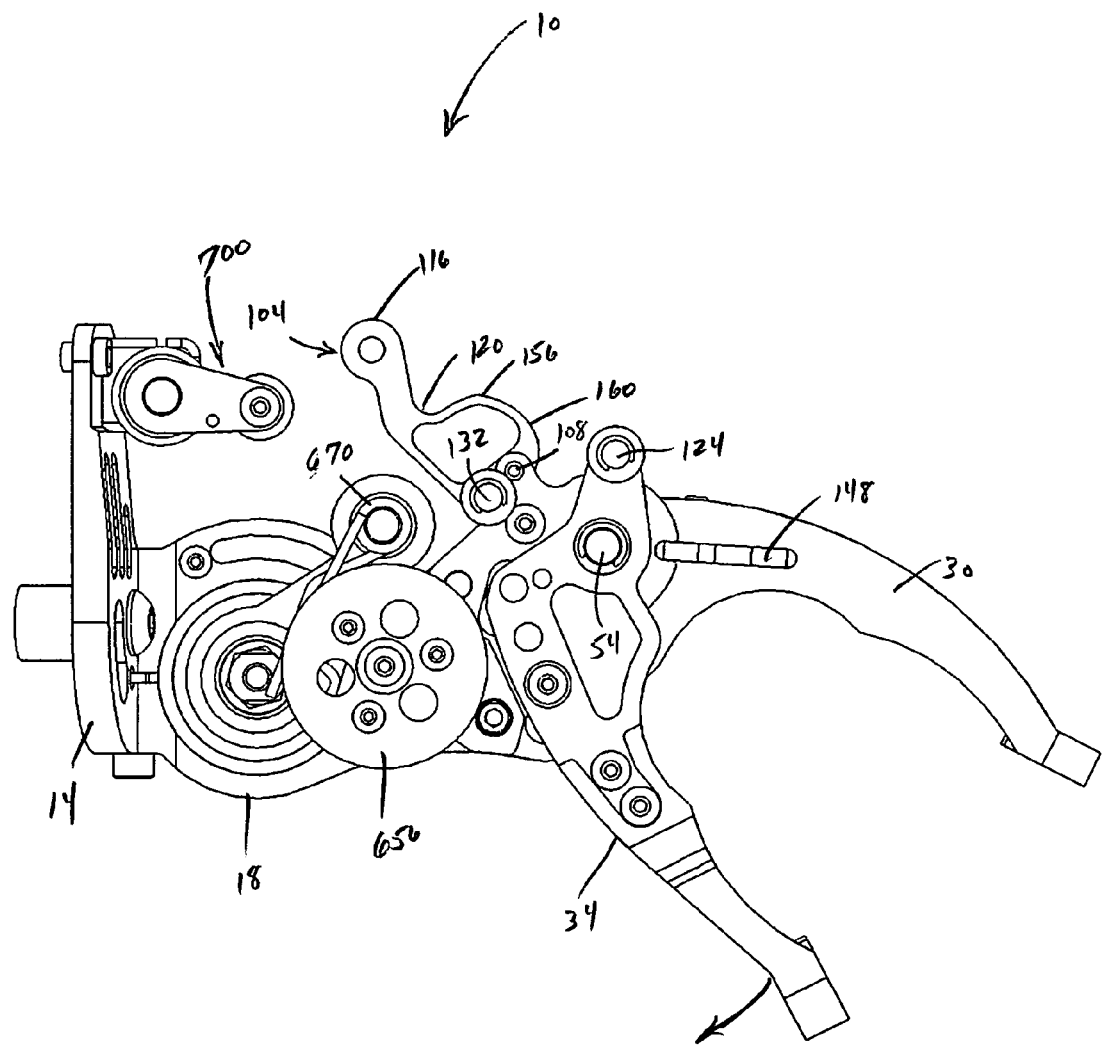
FIG. 20 is a side elevation view of the device shown in FIG. 19, wherein the device is in voluntary opening mode with the opening digit pulled open for grasping an object.

Referring now to FIG. 19, the cam switch 104 is rotated to the second position corresponding to the VO mode. In addition, the closing digit 30 is locked in place by aligning and pushing closing digit locking tab 148 into a locking tab receptacle 152. In the VO mode, the opening digit 34 is shut tight against the closing digit 30 because the elastic bands pull first and second tensioning rods 124 and 132 together. Although the closing digit 30 is locked, the opening digit 34 is able to move if sufficient tension is applied to the tendon 82 that is wrapped around tendon guide axle 86 at the rear portion 40 of the opening digit 34. As shown in FIG. 20, the opening digit 34 is pulled away from the closing digit 30 that is locked in place. Once an object is positioned between the digits in the VO mode, the tension is released in the input cable 682, thus clamping the object between the digits 26.

The shape of the cam switch 104 includes a sloped transition surface 156 between a base 160 and the pocket 120. This sloped transition surface 156 enables a gradual expansion of the elastic bands 140 as the prehensor 10 is switched from VO mode to VC mode. More particularly, when the prehensor 10 is in the VO mode, the opening digit 34 is under considerable pressure against the closing digit 30. In order to take up the tension in the elastic bands 140 and lock the opening digit 30 in place within the pocket 120 of the cam switch 104, the cam switch 104 is gradually rotated from its second position in VO mode to its first position in VC mode. During this rotation process, the sloped transition surface 156 slides against the first tensioning rod 124. As best seen in FIG. 5, to facilitate easier transitioning between the VO and VC modes, the center portion of the first tensioning rod 124 preferably includes an exterior rotatable cylinder 164.

The tension applied between the first and second tensioning rods 124 and 132 can be incrementally adjusted by adding additional bands 140. More particularly, if the device is for a child, the number of bands used may be less than for an adult man, because the adult man can typically generate more tension force in the prehensor 10 to pull the bands 140 in the VO mode.

In use, the VO/VC assembly 100 may be used to change between the VO mode to the VC mode, and to change from the VC mode back to the VO mode. Assuming the VO/VC assembly 100 is in the VO mode, a user changes to the VC mode by using cam lever arm 116 to rotate the cam switch 104 forward. During this action, the sloped transition surface 156 of the cam switch 104 contacts the first tensioning rod 124 or the exterior rotatable cylinder 164 positioned on the first tensioning rod 124, and the first tensioning rod 124 is moved from the base 160 of the cam switch 104 to the pocket 120 of the cam switch 104. This action also expands the bands 140 because the separation distance between the first tensioning rod 124 and the second tension rod 132 is increased. The opening digit 34 is locked in place because the first tension rod 124 that passes through the rear portion 40 of the opening digit 34 is locked within the pocket 120 of the cam switch 104. The closing digit 30 is then unlocked by releasing closing digit locking tab 148 from locking tab receptacle 152.

To change from the VC mode to the VO mode, the above-described process may reversed. Thus, to change to the VO mode the closing digit locking tab 148 is inserted into locking tab receptacle 152. This action locks the closing digit 30. The cam switch 104 is then rotated back, releasing the first tensioning rod 124 from the pocket 120 of the cam switch. This action releases the opening digit 34 to rotate, and by so doing, the opening digit 34 closes to contact the closing digit 30 because the tension in the bands 140 draws the opening digit 34 to the locked closing digit 30. The user of the prehensor 10 may then cause the opening digit 34 to separate from the closing digit 30 by applying a tension to the Bowden cable, which is transferred through the device to the tendon 82 that pulls the tendon guide axle 86 at the rear portion 40 of the opening digit 34. Once an object is positioned between the digits 26, the user releases the tension in the Bowden cable, and the opening digit 34 closes against the object.

Figure 21:
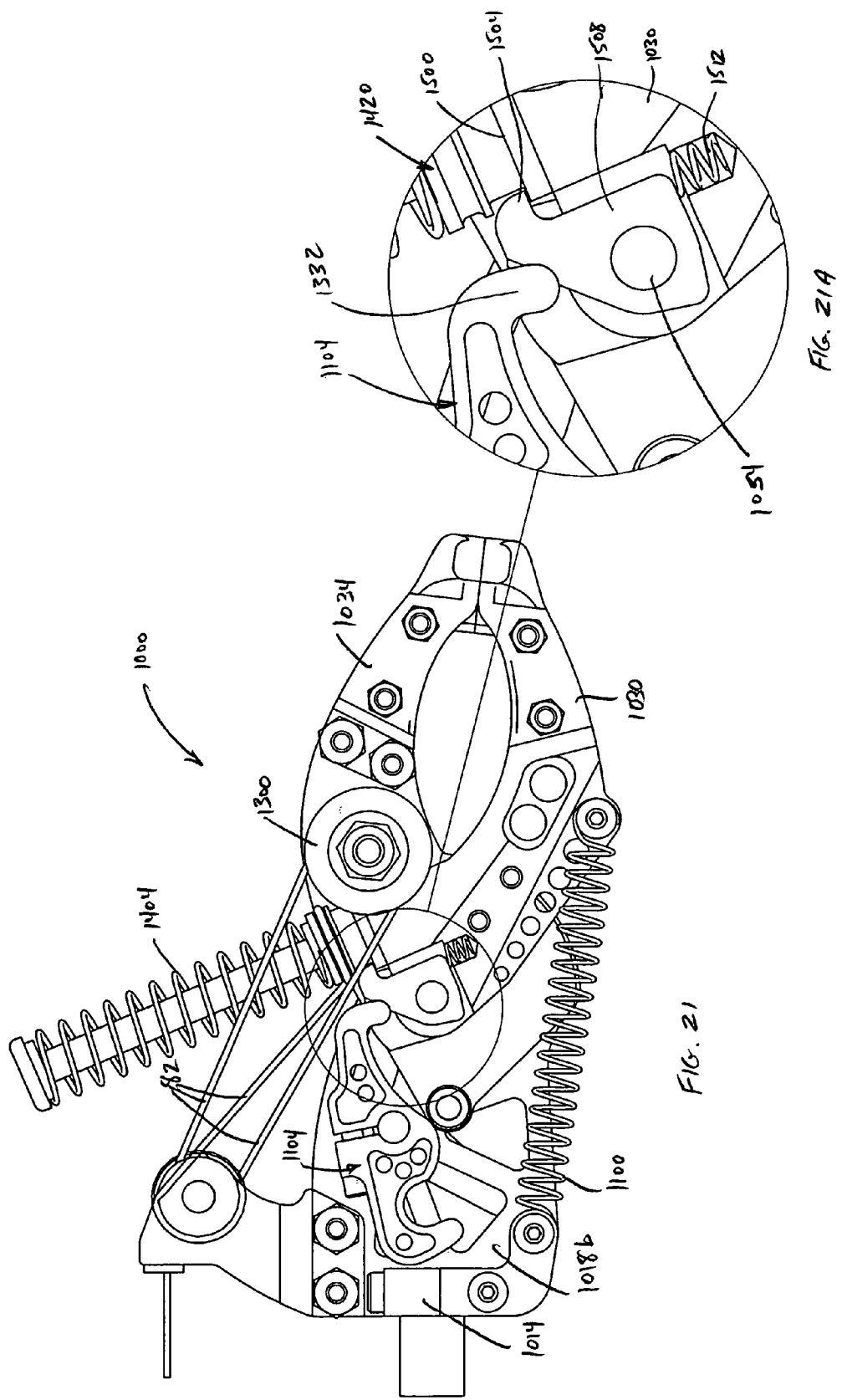
FIG. 21 is a side elevation view of the device shown in FIG. 10, excluding some components for clarity, wherein the device is in voluntary opening mode with the opening digit fully closed.

Referring now to FIG. 21, in accordance with embodiments of the present invention, the prehensor 1000 may include a selectable voluntary opening/voluntary closing ("VO/VC") assembly. As described above, using latch handle 1112, the latch 1104 can be rotated from a first position corresponding to the VC mode to a second position corresponding to a VO mode. When placed in the second position for VO mode, the latch first end 1312 disengages from the opening digit lock axle 1320, thus allowing the opening digit 1034 to move. In addition, the second end angled portion 1332 of the latch second end 1328 engages the indentation 1444 in at least one of the closing digit side plates 1428. Upon engaging the indentation 1444, the latch 1104 prevents the closing digit from rotating. Furthermore, as shown in FIGS. 21 and 21A, the latch second end angled portion 1332 urges the bushing catch 1504 of closing digit lock 1508 over the bushing flange 1500, thereby locking the VMA bushing 1420 in place in the VO mode. With both the closing digit 1030 and the VMA bushing 1420 locked, the opening digit 1034 is able to move when the tendon 82 applies a pulling force on opening digit pulley 1300.

Figure 22:
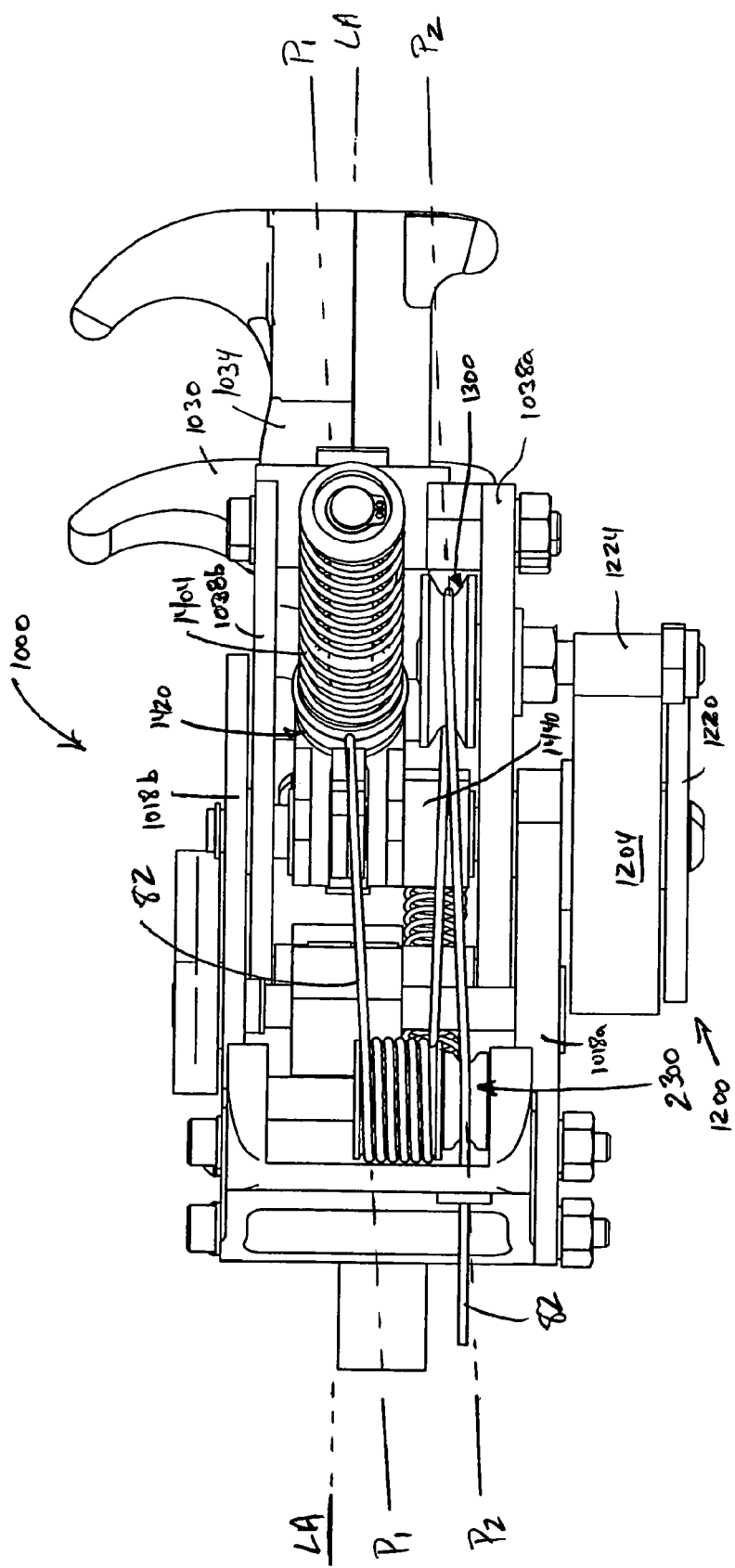
FIG. 22 is a top plan view of the device shown in FIG. 10 illustrating the position of the tendon within the device.

As shown in FIG. 22, in accordance with embodiments of the present invention, the tendon 82 acts on two planes within the prehensor 1000. More particularly, a pulley and passive holding assist clutch assembly 2300 interconnected to the base member 1014, along with spacer 1440, serve to align the tendon 82 along two planes depending upon which mode the prehensor 1000 is in. Although tension exists along the entire length of the tendon 82 in either the VO or VC mode, in the VC mode the tendon 82 applies a force to the bushing 1420 along plane P1-P1, and in VO mode the tendon 82 applies a force to the pulley 1300 along plane P2-P2. The planes P1-P1 and P2-P2 more closely parallel the longitudinal axis LA-LA of the prehensor 1000 than if the multiple wrappings were not used on the pulley and passive holding assist clutch assembly 2300. Thus, the tension applied by tendon 82 is more efficient. In addition, the multiple wrappings of the tendon 82 leading to the pulley and passive holding assist clutch assembly 2300 allows the tension to be reduced slightly without the pulley portion of the assembly 2300 rotating. This maintains the tension in the forward portion of the prehensor 1000 when the input tension in the tendon 82 is relaxed slightly.

Figure 23:
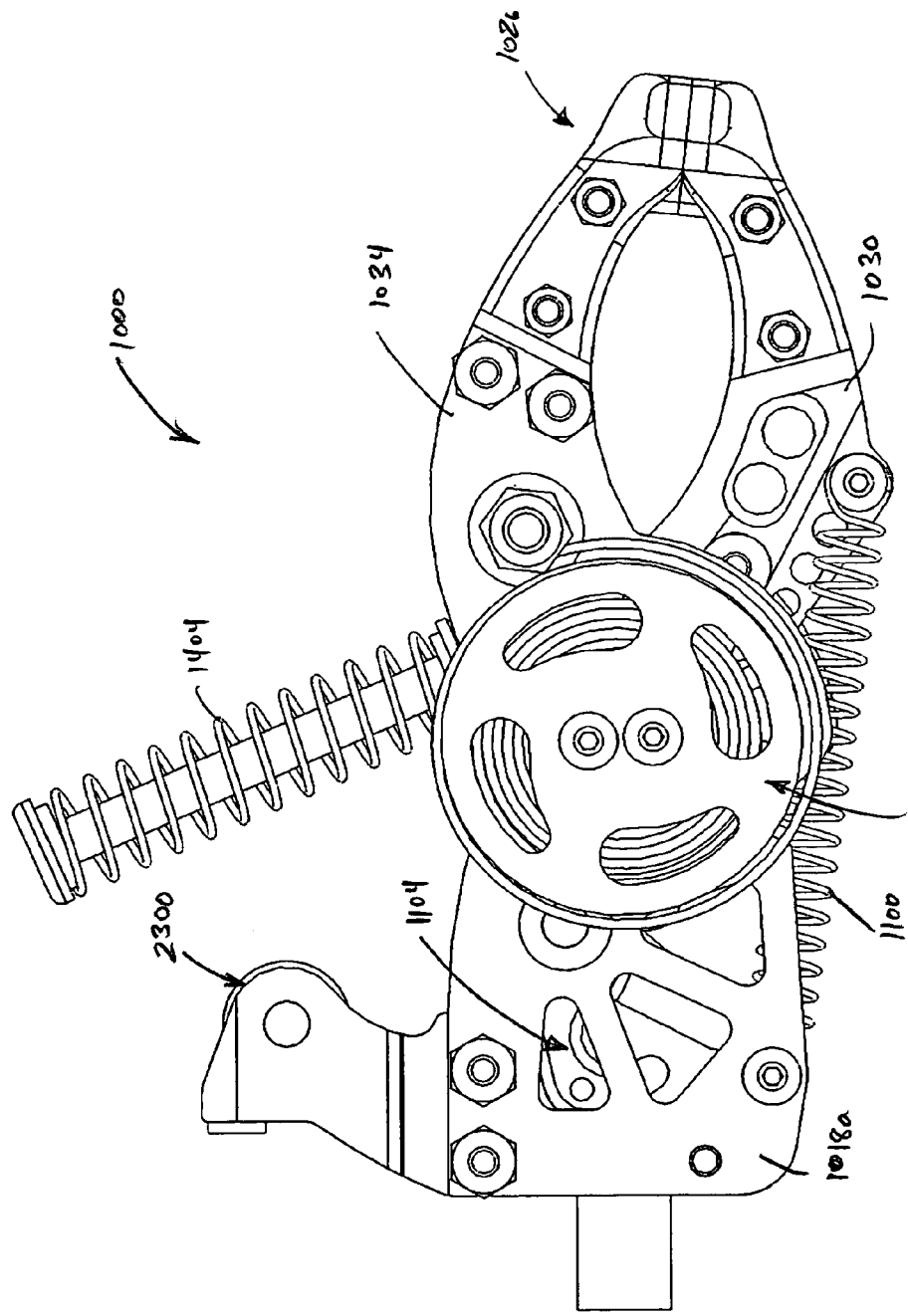
FIG. 23 is a side elevation view of the device shown in FIG. 10, excluding the tendon for clarity, wherein the device is in a voluntary opening mode with the opening digit closed against the closing digit, and showing the opening digit biasing assembly interconnected to the opening digit.

Referring now to FIG. 23, a side elevation view of the prehensor 1000 is shown with the latch 1104 in its second position and the digits 1026 closed. As noted above, clock spring 1204 is interconnected to both the longitudinal member 1018a and the first opening digit forked member 1038a. Therefore, as tension is added to the tendon 82, in order to move the opening digit 1034, sufficient tension must be applied to first overcome the prior set resistance of the clock spring 1204.

Figure 24:
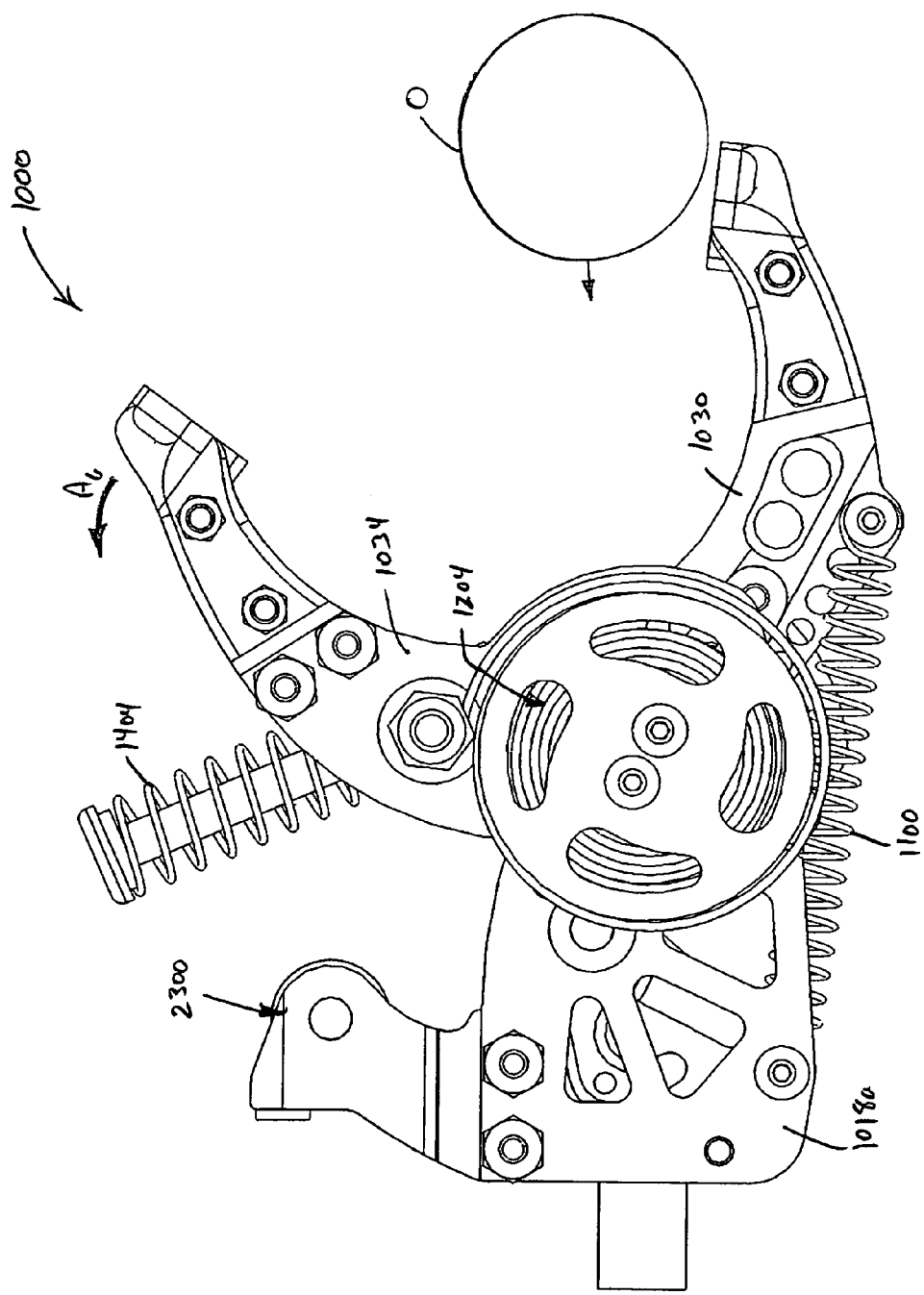
FIG. 24 is the same side elevation view as shown in FIG. 23, but with the opening digit retracted from the closing digit.

Referring now to FIG. 24, the prehensor 1000 is depicted with the opening digit 1034 rotated in direction of arrow A6, thus separating the digits. An object O can then be placed between the digits 1030 and 1034, the input tension released, and the passive state of the VO mode thereafter constantly applies a gripping force consistent with the prior set resistance of the clock spring 1204.

The VO/VC assembly offers the advantage of using a clock spring 1204 instead of elastic or rubber bands. Therefore, a clock spring 1204 made of a material such as stainless steel can be washed and is not susceptible to the same corrosive materials, such as weathering or gasoline, that would harm elastic or rubber bands.

It should be understood that a clock spring 1204 may be adapted for use in a VO/VC assembly for prehensor 10, and such device is within the scope of the present invention.

In use, the VO/VC assembly of prehensor 1000 may be used to change between the VO mode to the VC mode, and to change from the VC mode back to the VO mode. Assuming the prehensor 1000 is in VO mode, a user changes to the VC mode by using the latch handle 1112 to rotate the latch 1104 back. When the latch 1104 is moved back, the second end angled portion 1332 disengages from the indentation 1444, thereby releasing the closing digit 1030. In addition, closing digit lock spring 1512 urges the closing digit lock 1508 to move, thus disengaging the bushing catch 1504 from the bushing flange 1500. This allows the tendon 82 to move the bushing 1420. The opening digit 1034 is locked because the latch first end 1312 engages and secures the opening digit lock axle 1320 within the pocket region 1318. Thus, the closing digit 1030 is able to rotate when a tension is input into tendon 82.

To change from the VC mode to the VO mode, the above-described process may reversed. Accordingly, a user changes to the VC mode by using latch handle 1112 to rotate the latch 1104 forward. When the latch 1104 is in its forward position, the second end angled portion 1132 engages the indentation 1444 in at least one of the closing digit side plates 1428. Upon engaging the indentation 1444, the latch prevents the closing digit 1030 from rotating. The position of the second end angled portion 1132 also urges the bushing catch 1504 of the closing digit lock 1508 over the bushing flange 1500, thereby locking the VMA bushing 1420 in place in the VO mode. This prevents the tendon 82 from moving bushing 1420. The opening digit 1034 is allowed to rotate in VO mode because when the latch 1104 is rotated forward, the latch first end 1312 rotates back and disengages the pocket region 1318 from the opening digit lock axle 1320. The opening digit 1034 can be moved when a tension is input into tendon 82, pulling on opening digit pulley 1300. The user of the prehensor 1000 may then cause the opening digit 1034 to separate from the closing digit 1030 by applying a tension to the Bowden cable, which pulls the tendon 82 and displaces opening digit 1034 by pulling on pulley 1300. Once an object is positioned between the digits 1026, the user releases the tension in the Bowden cable, and the opening digit 1034 closes against the object.

Safety Clutch

Figure 25:
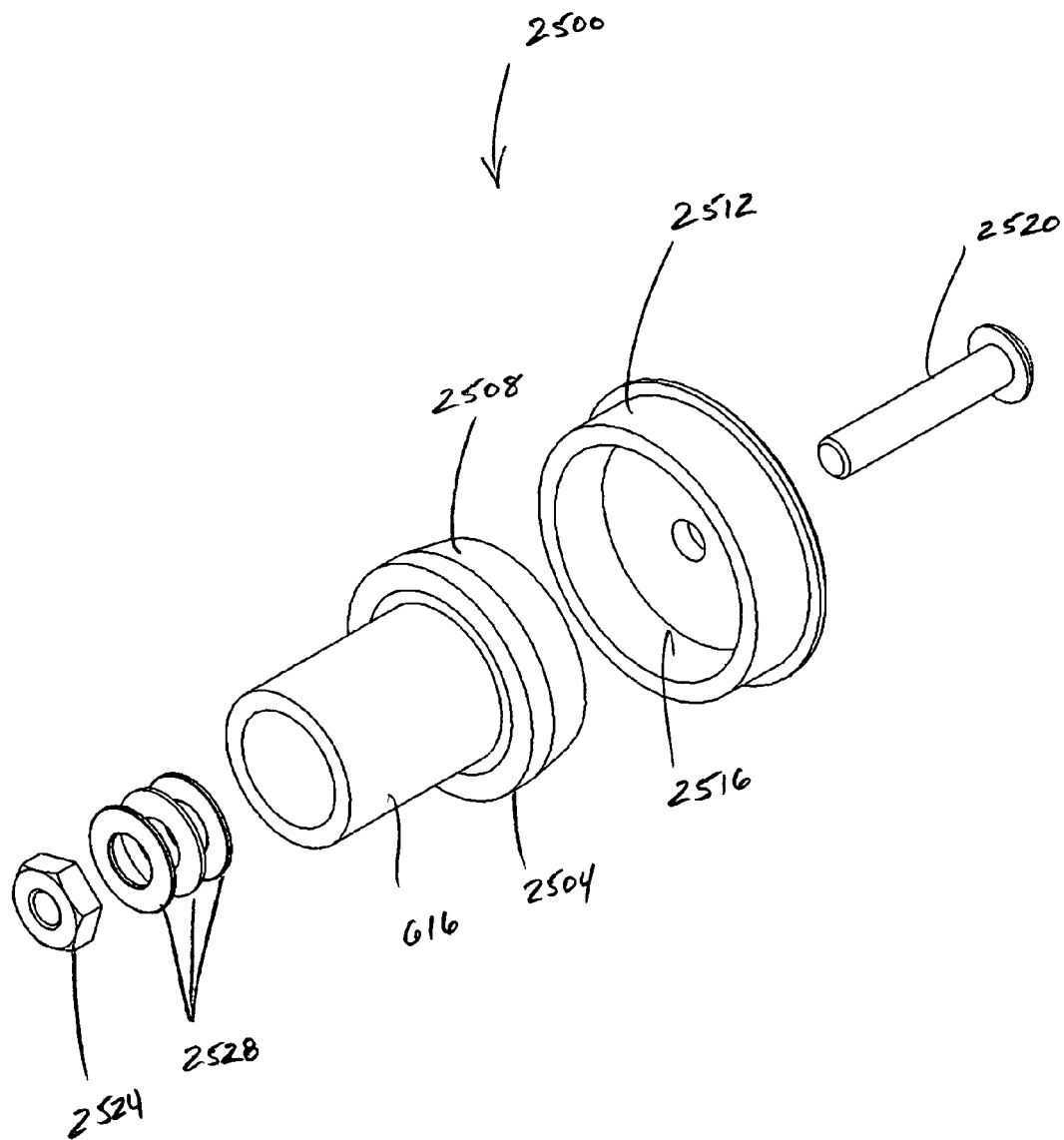
FIG. 25 is a side perspective view of a safety clutch mechanism in accordance with embodiments of the present invention.
Figure 25A:
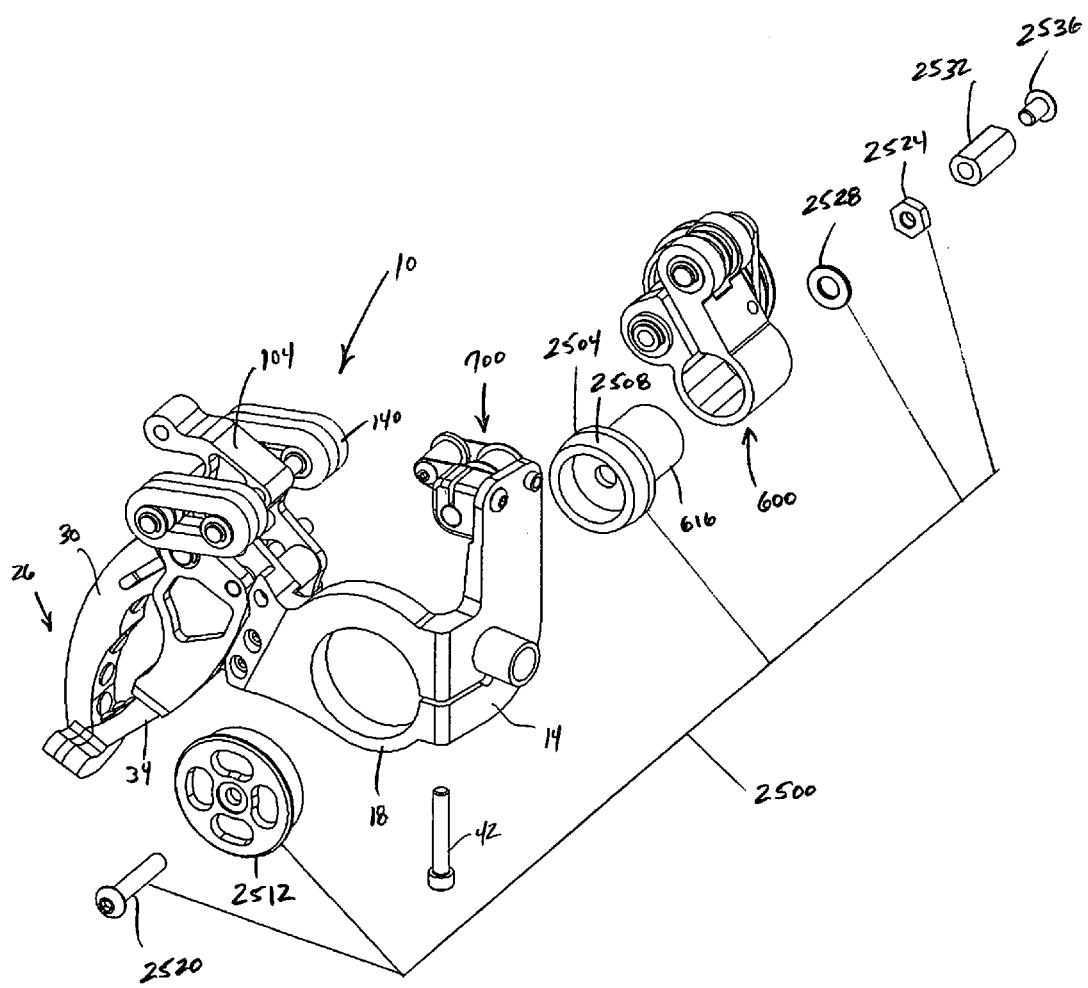
FIG. 25A is a partially exploded perspective view of the device shown in FIG. 1 further comprising the device shown in FIG. 25.

Referring now to FIGS. 25 and 25A, in accordance with embodiments of the present invention, a prehensor may include a safety clutch 2500. The safety clutch 2500 is an overload protection device that releases the digits from an object if sufficient force is applied between the closed digits. Once excess torque is relieved through slippage, the clutch re-seats undamaged and is again ready for continued service.

The safety clutch 2500 is configured to be in force communication with at least one of the digits 26 of a prehensor. For the device shown in FIG. 25, the safety clutch 2500 is interconnected to the brake assembly 600. Alternatively, it may be interconnected to the block axle 1840 of the VMA block assembly. Thus, it is to be understood that the safety clutch 2500 has application to a variety of prehensor configurations.

In accordance with embodiments of the present invention, the safety clutch 2500 comprises a first clutch member 2504 interconnected to rotatable structure linked or otherwise connected to one of the digits 26, such as the cylindrical drum 616 of brake assembly 600. The first clutch member 2504 includes sloped or first conical shaped surface 2508. The first clutch member 2504 is in communication with a second clutch member 2512. The second clutch member 2512 includes a sloped or second conical shaped surface 2516. When assembled, at least a portion of the first conical shaped surface 2508 contacts at least a portion of the second conical shaped surface 2516.

In accordance with embodiments of the invention, the first clutch member 2504 is placed into communication with the second clutch member 2504 by inserting a connector 42 such as a bolt 2520 through the portions 2504 and 2512. Preferably a means for biasing is placed along the bolt 2520 prior to tightening the assembly using a nut 2524. In one embodiment, the means for biasing comprises a plurality of Belleville spring washers 2528. The torque force necessary to rotate the surfaces 2508 and 2516 relative to each other, and thereby release the digits, is set by adjusting the pressure applied between the surfaces after they are assembled. Maximum torque limits are pre-set by adjusting the initial compression of the spring washers 2528.

The surfaces 2508 and 2516 do not have to be conical. More particularly, the surfaces 2508 and 2516 may comprises other shapes, and may further comprises ridges or texturing on the surfaces.

The safety clutch 2500 of the present invention is distinguishable from other safety means that would need to be reset, such as a pin that shears under a given load.

Referring again to FIG. 25A, in accordance with embodiments of the present invention, the safety clutch 2500 is interconnected to the brake assembly 600 of prehensor 10. When used with the brake assembly 600, a drum spacer 2532 and screw and washer 2536 are preferably interconnected to the safety clutch assembly 2500. In addition, the upon assembly, the second spring leg of detent spring 676 is placed against the screw and washer 2536 adjacent the drum spacer 2532. In this embodiment, when the maximum torque limit is reached with the safety clutch 2500, the brake assembly 600, drum 616 and first clutch member 2504 rotate relative to the second clutch member 2512, thereby releasing the digits 26.

In use, a user of a prehensor with a safety clutch 2500 uses the prehensor to hold an object. If while holding the object the force between the digits creates a force that translates within the prehensor to a torque that exceeds the maximum preset torque of the safety clutch 2500, the first conical shaped surface 2508 of the first clutch member 2504 rotates against the second conical shaped surface 2516 of the second clutch member 2512. The rotatable digit that is interconnected to the safety clutch 2500 is then released, and the prehensor is disengaged from the object. The maximum preset torque is adjustable using spring washers 2528 and a bolt 2520 to compress the first conical shaped surface 2508 of the first clutch member 2504 against the second conical shaped surface 2516 of the second clutch member 2512.

Replaceable Digit Portions

Figure 26:
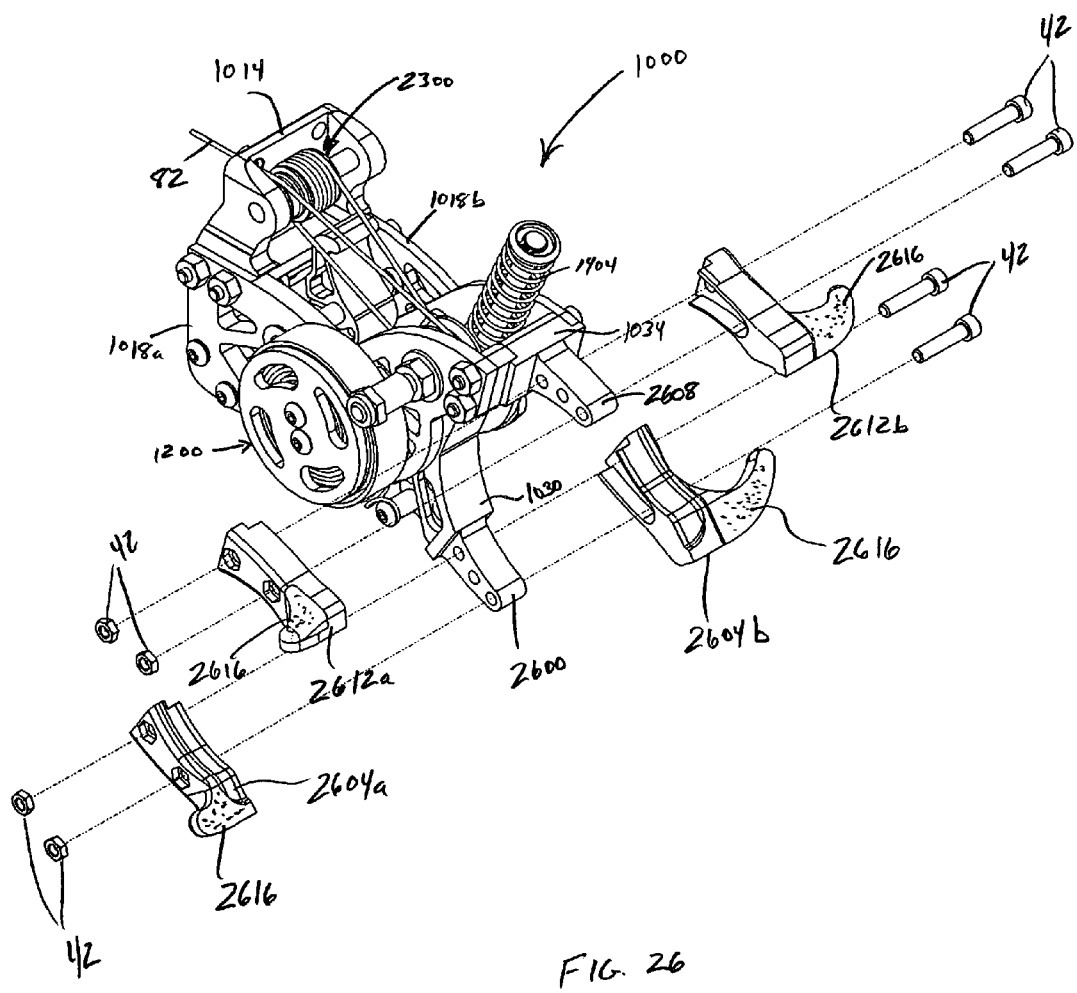
FIG. 26 is a partially exploded perspective view of the device shown in FIG. 10, illustrating replaceable digits in accordance with embodiments of the present invention.

Referring now to FIG. 26, in accordance with embodiments of the present invention, the digits 26 may include replaceable digit portions. More particularly, for the digits 1030 and 1034 shown in FIG. 26, the closing digit 1030 includes a closing digit tang 2600, to which is attached replaceable digit members 2604a and 2604b. The opening digit includes opening digit tang 2608, to which is attached replaceable digit members 2612a and 2612b. Although shown with two replaceable digit portions per digit, the replaceable digit portions may be comprised of one or any number of pieces. Furthermore, the illustration of replaceable digits for prehensor 1000 is for purposes of providing an example. It is to be understood that replaceable digit portions are contemplated for prehensor 10 described herein, as well as for other prehensor devices not described in this document.

Self-Decontaminating Digits

Referring still to FIG. 26, in accordance with embodiments of the present invention, the digits may comprise a self-decontaminating material. For example, the digits may include a layer or be impregnated with photo-catalytic agents 2616, such as titanium dioxide. For example, the replaceable digit members 2604a, 2604b, 2612a and 2612b may be made of molded plastics impregnated with titanium dioxide. Once exposed to UV light, the photo-catalytic agent 2616 kills off bacteria and viruses that contact the surface of the photo-catalytic agent.

Tendon

Figure 27:
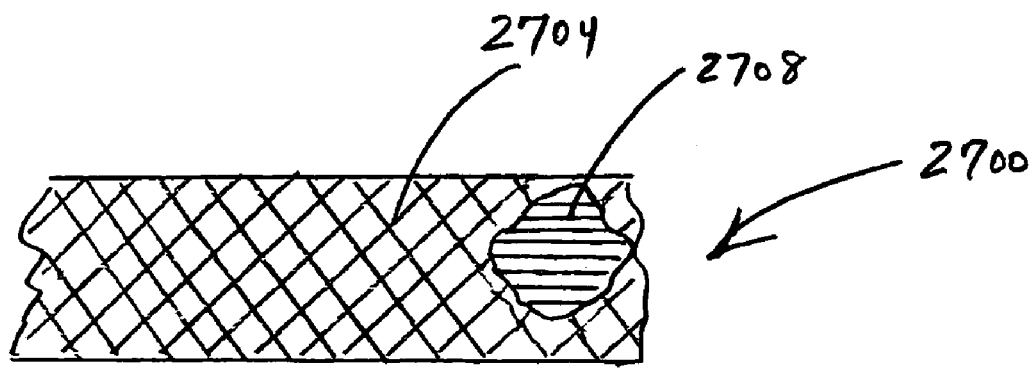
FIG. 27 is a side elevation view with a partial cut-away, FIG. 27 showing a tendon in accordance with embodiments of the present invention.
Figure 27A:
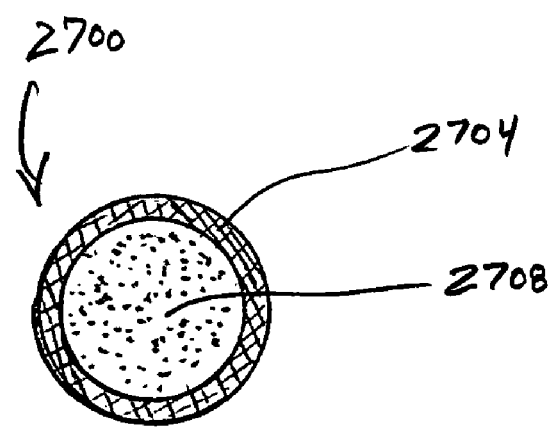
FIG. 27A is an end view of the tendon shown in FIG. 27.

In a separate aspect of the invention, an improved tendon for a prehensor is provided. Referring now to FIGS. 27 and 27A, the tendon 2700 comprises an exterior portion or jacket 2704 and an interior portion or core 2708. The jacket 2704 serves to protect the core 2708 from abrasion, and also provides an exterior surface for the tendon 2700 that has low friction characteristics. In one embodiment, the jacket 2704 comprises a braided structure of SPECTRA®; however, the structure of the jacket 2704 may take on other forms. The core 2708 preferably comprises a material that has a high tensile strength with low creep characteristics and is able to remain structurally intact without kinking when used with relatively small pulleys or axles requiring a small radius of curvature. For tendon 2700, the core 2708 preferably comprises longitudinally oriented strands made of a liquid crystal polymer, such as VECTRAN®.

Although SPECTRA® by itself tends to creep, requiring readjustment if used as the sole material for the tendon, it has low friction characteristics that match particularly well to providing a jacket 2704 for the core 2708 of VECTRAN® that resists creep, but has high friction characteristics. Thus, the novel combination of a tendon 2700 having a jacket 2704 made of braided SPECTRA® and a core 2708 of strands of VECTRAN® has been found to provide good combined performance as a prehensor tendon. For prehensors 10 and 1000 presented in this document, although not required, a tendon 2700 having a jacket 2704 made of braided SPECTRA® and a core 2708 of strands of VECTRAN® is preferred for use as the tendon 82 shown in the figures and described in the text.

A number of variations and modifications of the invention(s) can be used. It would be possible to provide for some features of the invention without providing others. For example, in one alternative embodiment, a VMA mechanism is used without a selectable VO/VC mechanism; that is, a VMA mechanism in a voluntary closing device without voluntary opening capability. As another example, in another alternative embodiment, a safety clutch is used in a voluntary closing device without voluntary opening capability. Accordingly, a number of different combinations are possible, and the preceding two examples are for illustrative purposes only.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description Of The Invention for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description Of The Invention, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A prehensor device used for engaging an object, the prehensor device operated by a source of tensile force, the prehensor device comprising:
    (a) a base member;
    (b) at least one longitudinal member engaging said base member;
    (c) at least first and second digits, said first and second digits engaging said longitudinal member;
    (d) a rotatable biasing member engaging at least one of (i) said first digit and (ii) said longitudinal member, wherein said biasing member comprises a bushing; and
    (e) a tendon interconnected to the source of tensile force and said biasing member, wherein said tendon is interconnected to said bushing;
    wherein, to provide a first mechanical advantage, at least a first tension is applied using the source of tensile force to rotate said biasing member and said first digit whereby the object is sized between said first and second digits, wherein, to provide a second mechanical advantage, at least a second tension is applied using the source of tensile force to compress said biasing member, whereby a grip pressure is applied to the object, and wherein the first tension is less than the second tension.

2. The device as claimed in claim 1, wherein:
said second digit comprises a locking axle; and
said tendon is interconnected to said first and second digits; and further comprising
    (f) a rotatable locking member engaging said longitudinal member, wherein said locking member may be positioned for selectively choosing a voluntary closing mode or a voluntary opening mode;
    wherein said locking member is placed in a first position for said voluntary closing mode, wherein said locking member secures said locking axle, wherein said first digit is separated from said second digit and said first tension is applied using the source of tensile force to rotate said biasing member and said first digit whereby the object is sized between said first and second digits; and
    wherein said locking member is placed in a second position for said voluntary opening mode, wherein said first digit is substantially adjacent said second digit and a third tension is applied using the source of tensile force to separate said second digit from said first digit, and wherein the third tension is reduced to engage the object between the first and second digits.

3. The device as claimed in claim 1, further comprising:
    (f) a safety clutch interconnected to at least one of said first or second digits, the safety clutch comprising:
        (i) a first clutch member including a first contacting surface;
        (ii) a second clutch member including a second contacting surface, said second clutch member fixedly secured to said longitudinal frame member, at least a portion of said first contacting surface communicating with said second contacting surface;
        (iii) an adjustable connector for biasing said first clutch member against said second clutch member; and
        (iv) a clutch biasing member operatively associated with said adjustable connector, wherein said adjustable connector further operates to adjust the bias force between said first contacting surface and said second contacting surface as applied by the clutch biasing member, wherein a minimum torque is needed to rotate said first clutch member relative to said second clutch member;
    wherein, when a separation force is applied between the first and second digits, said first clutch member will rotate relative to said second clutch member when said separation force causes a reaction torque between said first clutch member and said second clutch member that exceeds said minimum torque.

4. The device as claimed in claim 1, wherein at least one of said first and second digits comprises:
    (f) a replaceable digit comprising:
        (i) a tang portion; and
        (ii) a replaceable digit portion detachably interconnected to said tang portion.

5. The device as claimed in claim 1, wherein at least one of said first and second digits comprises a self-decontaminating material comprising a photo-catalytic agent.

6. The device as claim in claim 1, wherein said biasing member further comprises a coil spring.

7. A prehensor device used for engaging an object, the prehensor device operated by a source of tensile force, the prehensor device comprising
    (a) a base member;
    (b) at least one longitudinal member engaging said base member;
    (c) at least first and second digits, said first and second digits engaging said longitudinal member, said first digit comprising a locking axle;
    (d) a tendon interconnected to the source of tensile force and to said first and second digits; and
    (e) a rotatable locking member engaging said longitudinal member, wherein said locking member may be positioned for selectively choosing a voluntary closing mode or a voluntary opening mode;
    wherein said locking member is placed in a first position for said voluntary closing mode, wherein said locking member secures said locking axle, wherein said first digit is separated from said second digit and a first tension is applied using the source of tensile force to close said second digit against at least one of (i) said first digit and (ii) the object; and
    wherein said locking member is placed in a second position for said voluntary opening mode wherein said first digit is substantially adjacent said second digit and a second tension is applied using the source of tensile force to separate said second digit from said first digit, and wherein the second tension is reduced to engage the object between the first and second digits.

8. The device as claimed in claim 7, further comprising:
    (f) a rotatable biasing member engaging at least one of (i) said second digit and (ii) said longitudinal member, wherein said tendon is interconnected to said biasing member;
    wherein, to provide a first mechanical advantage, at least a first tension is applied using the source of tensile force to rotate said biasing member and said second digit whereby the object is sized between said first and second digits, wherein, to provide a second mechanical advantage, at least a second tension is applied using the source of tensile force to compress said biasing member, whereby a grip pressure is applied to the object, and wherein the first tension is less than the second tension.

9. The device as claimed in claim 8, wherein said biasing member comprises a bushing, wherein said tendon is interconnected to said bushing.

10. The device as claimed in claim 8, wherein said biasing member further comprises a coil spring.

11. The device as claimed in claim 7, further comprising:
(f) a safety clutch interconnected to at least one of said first or second digits, the safety clutch comprising:
  (i) a first clutch member including a first contacting surface;
  (ii) a second clutch member including a second contacting surface, said second clutch member fixedly secured to said longitudinal frame member, at least a portion of said first contacting surface communicating with said second contacting surface;
  (iii) an adjustable connector for biasing said first clutch member against said second clutch member; and
  (iv) a clutch biasing member operatively associated with said adjustable connector, wherein said adjustable connector further operates to adjust the bias force between said first contacting surface and said second contacting surface as applied by the clutch biasing member, wherein a minimum torque is needed to rotate said first clutch member relative to said second clutch member;
wherein, when a separation force is applied between the first and second digits, said first clutch member will rotate relative to said second clutch member when said separation force causes a reaction torque between said first clutch member and said second clutch member that exceeds said minimum torque.

12. The device as claimed in claim 7, wherein at least one of said first and second digits comprises:
(f) a replaceable digit comprising:
  (i) a tang portion; and
  (ii) a replaceable digit portion detachably interconnected to said tang portion.

13. The device as claimed in claim 7, wherein at least one of said first and second digits comprises a self-decontaminating material comprising photo-catalytic agent.

14. The device as claimed in claim 7, further comprising:
(f) a brake member engaging said longitudinal member, said brake member comprising a pulley rotatable about an axle interconnected to said brake member, wherein said tendon engages said brake member; and
(g) an input cable interconnected to said source of tensile force and engaging said pulley;
wherein, to provide a first mechanical advantage, said locking member is placed in said first position and said first tension applied using the source of tensile force pulls said input cable and causes said brake member to rotate relative to said longitudinal member while said pulley remains substantially stationary relative to said brake member whereby said tendon is pulled and said second digit is rotated for sizing the object between said first and second digits, and wherein, to provide a second mechanical advantage, at least a third higher tension is applied using the source of tensile force pulling said input cable and causing said pulley to rotate relative to said brake member while said brake member remains substantially stationary relative to said longitudinal member whereby a grip pressure is applied to the object.

15. The device as claimed in claim 7, wherein said locking member further comprises a pocket for securing said locking axle.

16. A prehensor device used for engaging an object, the prehensor device operated by a source of tensile force, the prehensor device comprising:
(a) a base member;
(b) at least one longitudinal member engaging said base member;
(c) at least first and second digits, said first and second digits engaging said longitudinal member, said second digit comprising a locking axle;
(d) a rotatable biasing member engaging at least one of (i) said first digit and (ii) said longitudinal member; and
(e) a tendon interconnected to the source of tensile force and said biasing member, wherein said tendon is interconnected to said first and second digits;
wherein, to provide a first mechanical advantage, at least a first tension is applied using the source of tensile force to rotate said biasing member and said first digit whereby the object is sized between said first and second digits, wherein, to provide a second mechanical advantage, at least a second tension is applied using the source of tensile force to compress said biasing member, whereby a grip pressure is applied to the object, and wherein the first tension is less than the second tension;
(f) a rotatable locking member engaging said longitudinal member, wherein said locking member may be positioned for selectively choosing a voluntary closing mode or a voluntary opening mode;
wherein said locking member is placed in a first position for said voluntary closing mode, wherein said locking member secures said locking axle, wherein said first digit is separated from said second digit and said first tension is applied using the source of tensile force to rotate said biasing member and said first digit whereby the object is sized between said first and second digits; and
wherein said locking member is placed in a second position for said voluntary opening mode, wherein said first digit is substantially adjacent said second digit and a third tension is applied using the source of tensile force to separate said second digit from said first digit, and wherein the third tension is reduced to engage the object between the first and second digits.

17. The device as claimed in claim 16, wherein at least one of said first and second digits comprises:
(g) a replaceable digit comprising:
  (i) a tang portion; and
  (ii) a replaceable digit portion detachably interconnected to said tang portion.

18. The device as claimed in claim 16, wherein at least one of said first and second digits comprises a self-decontaminating material comprising a photo-catalytic agent.

19. A prehensor device used for engaging an object, the prehensor device operated by a source of tensile force, the prehensor device comprising:
(a) a base member;
(b) at least one longitudinal member engaging said base member;
(c) at least first and second digits, said first and second digits engaging said longitudinal member;

(d) a rotatable biasing member engaging at least one of (i) said first digit and (ii) said longitudinal member; and (e) a tendon interconnected to the source of tensile force and said biasing member;

wherein, to provide a first mechanical advantage, at least a first tension is applied using the source of tensile force to rotate said biasing member and said first digit whereby the object is sized between said first and second digits, wherein, to provide a second mechanical advantage, at least a second tension is applied using the source of tensile force to compress said biasing member, whereby a grip pressure is applied to the object, and wherein the first tension is less than the second tension;

(f) a safety clutch interconnected to at least one of said first or second digits, the safety clutch comprising:
 (i) a first clutch member including a first contacting surface;
 (ii) a second clutch member including a second contacting surface, said second clutch member fixedly secured to said longitudinal frame member, at least a portion of said first contacting surface communicating with said second contacting surface;
 (iii) an adjustable connector for biasing said first clutch member against said second clutch member; and
 (iv) a clutch biasing member operatively associated with said adjustable connector, wherein said adjustable connector further operates to adjust the bias force between said first contacting surface and said second contacting surface as applied by the clutch biasing member, wherein a minimum torque is needed to rotate said first clutch member relative to said second clutch member;

wherein, when a separation force is applied between the first and second digits, said first clutch member will rotate relative to said second clutch member when said separation force causes a reaction torque between said first clutch member and said second clutch member that exceeds said minimum torque.

20. The device as claimed in claim 19, wherein at least one of said first and second digits comprises:
 (g) a replaceable digit comprising:
  (i) a tang portion; and
  (ii) a replaceable digit portion detachably interconnected to said tang portion.

21. The device as claimed in claim 19, wherein at least one of said first and second digits comprises a self-decontaminating material comprising a photo-catalytic agent.

* * * * *